United States Patent
Shoemaker et al.

(10) Patent No.: US 10,851,412 B2
(45) Date of Patent: Dec. 1, 2020

(54) CELL POTENCY ASSAY FOR THERAPEUTIC POTENTIAL

(71) Applicant: FATE THERAPEUTICS, INC., San Diego, CA (US)

(72) Inventors: Daniel Shoemaker, San Diego, CA (US); David L. Robbins, Temecula, CA (US)

(73) Assignee: Fate Therapeutics, Inc., San Diego, CA (US)

( * ) Notice: Subject to any disclaimer, the term of this patent is extended or adjusted under 35 U.S.C. 154(b) by 860 days.

(21) Appl. No.: 14/205,161

(22) Filed: Mar. 11, 2014

(65) Prior Publication Data

US 2015/0064139 A1    Mar. 5, 2015

Related U.S. Application Data

(60) Provisional application No. 61/789,717, filed on Mar. 15, 2013.

(51) Int. Cl.
*A61K 35/28*    (2015.01)
*C12Q 1/6876*   (2018.01)
*C12Q 1/6881*   (2018.01)

(52) U.S. Cl.
CPC ............ *C12Q 1/6876* (2013.01); *A61K 35/28* (2013.01); *C12Q 1/6881* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 5,077,049 A | 12/1991 | Dunn et al. | |
| 5,397,706 A | 3/1995 | Correa et al. | |
| 5,442,033 A | 8/1995 | Bezwada | |
| 5,460,964 A | 10/1995 | McGlave et al. | |

(Continued)

FOREIGN PATENT DOCUMENTS

| | | |
|---|---|---|
| CA | 2743255 | 6/2010 |
| EP | 0927552 | 9/2003 |

(Continued)

OTHER PUBLICATIONS

Adams et al., "Haematopoietic stem cells depend on Gαs-mediated signalling to engraft bone marrow," Nature, 459:103-107 (2009).

(Continued)

*Primary Examiner* — Renee Claytor
*Assistant Examiner* — Trent R Clarke
(74) *Attorney, Agent, or Firm* — Jones Day

(57) ABSTRACT

The invention provides cell potency assays for measuring, determining, identifying, confirming, or validating the therapeutic potential of a cell population. Cell potency assays may be performed with various types of cells, including stem or progenitor cells, such as, for example, hematopoietic stem or progenitor cells. Cell potency assays may also be performed on stem or progenitor cells that have been treated with one or more agents to enhance therapeutic potential. Hematopoietic cells having therapeutic potential are useful in downstream clinical applications for increasing engraftment, reconstitution, homing, and proliferation in vivo.

20 Claims, 3 Drawing Sheets

(56) References Cited

U.S. PATENT DOCUMENTS

| | | | |
|---|---|---|---|
| 5,635,387 A | 6/1997 | Fei et al. | |
| 5,648,331 A | 7/1997 | Koudsi et al. | |
| 5,677,136 A | 10/1997 | Simmons et al. | |
| 5,709,472 A | 1/1998 | Prusik et al. | |
| 5,716,827 A | 2/1998 | Tsukamoto et al. | |
| 5,750,397 A | 5/1998 | Tsukamoto et al. | |
| 5,753,516 A | 5/1998 | Heagy et al. | |
| 5,759,793 A | 6/1998 | Schwartz et al. | |
| 5,854,033 A | 12/1998 | Lizardi | |
| 5,945,337 A | 8/1999 | Brown | |
| 6,191,109 B1 | 2/2001 | Besner et al. | |
| 6,207,802 B1 | 3/2001 | Zsebo et al. | |
| 6,610,719 B2 | 8/2003 | Paralkar et al. | |
| 6,747,037 B1 | 6/2004 | Old et al. | |
| 6,891,062 B2 | 5/2005 | Oida et al. | |
| 7,004,621 B2 | 2/2006 | Roberts et al. | |
| 7,131,958 B2 | 11/2006 | Deverre | |
| 7,147,626 B2 | 12/2006 | Goodman et al. | |
| 7,625,752 B2 | 12/2009 | Casper et al. | |
| 8,551,782 B2 | 10/2013 | Zon et al. | |
| 8,563,310 B2 | 10/2013 | Zon et al. | |
| 2002/0115586 A1 | 8/2002 | Enikolopov et al. | |
| 2003/0022363 A1 | 1/2003 | Rao et al. | |
| 2003/0096757 A1* | 5/2003 | Quirk | C07K 14/8146 514/8.1 |
| 2005/0054103 A1 | 3/2005 | Peled et al. | |
| 2005/0074435 A1 | 4/2005 | Casper et al. | |
| 2005/0101599 A1 | 5/2005 | Zeiher et al. | |
| 2005/0176140 A1 | 8/2005 | Benedict et al. | |
| 2006/0005153 A1 | 1/2006 | Maruyama et al. | |
| 2006/0121085 A1 | 6/2006 | Warren et al. | |
| 2006/0247214 A1 | 11/2006 | DeLong et al. | |
| 2007/0154563 A1 | 7/2007 | Behnam et al. | |
| 2008/0139865 A1 | 6/2008 | Galliher et al. | |
| 2009/0029912 A1 | 1/2009 | Gronthos et al. | |
| 2009/0220465 A1 | 9/2009 | Scadden et al. | |
| 2010/0143317 A1 | 6/2010 | Pecora et al. | |
| 2010/0173024 A1 | 7/2010 | McDaniel | |
| 2010/0322907 A1 | 12/2010 | Calvi et al. | |
| 2012/0004119 A1 | 1/2012 | Lenburg et al. | |
| 2012/0135878 A1 | 5/2012 | Lee et al. | |
| 2012/0189594 A1 | 7/2012 | Zon et al. | |
| 2012/0202288 A1 | 8/2012 | Mendlein et al. | |
| 2013/0136722 A1* | 5/2013 | Mahmud | A61K 35/28 424/93.7 |
| 2013/0209423 A1 | 8/2013 | Zon et al. | |
| 2013/0209424 A1 | 8/2013 | Zon et al. | |
| 2013/0216507 A1 | 8/2013 | Zon et al. | |
| 2014/0369972 A1 | 12/2014 | Shoemaker et al. | |

FOREIGN PATENT DOCUMENTS

| | | |
|---|---|---|
| EP | 1563846 | 8/2005 |
| JP | 05-149797 | 6/1993 |
| JP | 2005-220089 | 8/2005 |
| JP | 2009530408 | 8/2009 |
| RU | 2002113565 | 11/2000 |
| WO | WO 1995/06112 A1 | 3/1995 |
| WO | WO 1996/40866 A1 | 12/1996 |
| WO | WO 2000/38663 A2 | 7/2000 |
| WO | WO 2000/050568 A1 | 8/2000 |
| WO | WO 2001/12596 A1 | 2/2001 |
| WO | WO 2004/032965 A1 | 4/2004 |
| WO | WO 2004/078169 A1 | 9/2004 |
| WO | WO 2006/047476 A2 | 5/2006 |
| WO | WO 2006/078886 A2 | 7/2006 |
| WO | WO 2006/086639 A1 | 8/2006 |
| WO | WO 2007/070964 A1 | 6/2007 |
| WO | WO 2007/071456 A1 | 6/2007 |
| WO | WO 2007/092585 A2 | 8/2007 |
| WO | WO 2007/112084 A2 | 10/2007 |
| WO | WO 2008/021475 A2 | 2/2008 |
| WO | WO 2008/056963 A1 | 5/2008 |
| WO | WO 2008/073748 A1 | 6/2008 |
| WO | WO 2008/088379 A2 | 7/2008 |
| WO | WO 2009/104807 A1 | 8/2009 |
| WO | WO 2009/134532 A2 | 11/2009 |
| WO | WO 2010/054271 A1 | 5/2010 |
| WO | WO 2010/108028 A2 | 9/2010 |
| WO | WO 2012/021845 A2 | 2/2012 |
| WO | WO 2013/082241 A2 | 6/2013 |
| WO | WO 2013/082243 A1 | 6/2013 |

OTHER PUBLICATIONS

Attar et al., "Regulation of hematopoietic stem cell growth," Leukemia 18:1760-1768 (2004).

Barany, "Genetic disease detection and DNA amplification using cloned thermostable ligase," Proc. Natl. Acad. Sci. USA, 88(1):189-193 (1991).

Barker et al., "Mining the Wnt pathway for cancer therapeutics," Nat. Rev. Drug Discov., 5:997-1014 (2006).

Brandt et al., "Practical aspects of preparative HPLC in pharmaceutical and development production," LC-GC Europe, pp. 2-5 (2002).

Bug et al., "Valproic Acid Stimulates Proliferation and Self-renewal of Hematopoietic stem cells," Cancer Res., 65(7):2537-2541 (2005).

Capmany et al., "Short-term, serum-free, static culture of cord blood-derived CD34+ cells: effects of FLT3-L and MIP-1α on in vitro expansion of hematopoietic progenitor cells," Haematologica, 84:675-682 (1999).

Cayman Chemical Company, "16, 16-dimethyl Prostaglandin E2. Catalog No. 14750. CAS Registry No. 39746-25-3," Product Information, Mar. 30, 2006, one page.

Chen et al., "Intravenous administration of human umbilical cord blood reduces behavioral deficits after stroke in rats," Stroke, 32(11):2682-2688 (2001).

Cohn et al., "Crypt stem cell surivival in the mouse intestinal epithelium is regulated by prostaglandins synthesized through cyclooxygenase-1," J. Clin. Invest., 99(6):1367-1379 (1997).

Crawford, "Thoracoabdominal aortic aneurysms: Preoperative and intraoperative factors determining immediate and long-term results of operations in 605 patients," Vas. Surg. 3:389-404 (1986).

Curnow et al., "Topical Glucocorticoid Therapy Directly Induces Up-Regulation of Functional CXCR4 on Primed T Lymphocytes in the Aqueous Humor of Patients with Uveitis," J. Immunol., 172:7154-7161 (2004).

Daley, J P, et al., "Ex vivo expansion of human hematopoietic progenitor cells in serum-free StemProTM-34 Medium," Focus 18(3):62-67, 1996.

Davidson and Zon, "The 'definitive' (and 'primitive') guide to zebrafish hematopoiesis," Oncogene, 23:7233-7246, (2004).

De Jong and Zon, "Use of the zebrafish system to study primitive and definitive hematopoiesis," Annu. Rev. Genet., 39:481-501, (2005).

Desplat et al., "Is the COX-2 effect on accelerated hematopoiesis mediated by prostaglandin E2?" Exp. Hematol., 28:741-742 (2000).

Dupuis et al., "Prostaglandin E2 stimulates the growth of human blood CD34+ progenitors," Prostaglandins & Other Lipid Mediators, 55:179-186 (1998).

FDA +Sterile drug products produced by aseptic processing draft, 50 pages, Sep. 22, 2002.

FDA Guidance for Industry, Sterile drug products produced by aseptic processing—current good manufacturing practice, 63 pages (2003).

Fehér et al., "Prostagladin E2 as stimulator of haemopoietic stem cell proliferation," Nature, 247:550-551 (1974).

Freedman et al., "Autocrine and paracrine growth control by granulocyte-monocyte colony-stimulating factor of acute lymphoblastic leukemia cells," Blood, 81(11):3068-3075 (1993).

Galloway et al., "Ontogeny of hematopoiesis: examining the emergence of hematopoietic cells in the vertebrate embryo," Curr. Top. Dev. Biol., 53:139-158 (2003).

Gentile et al., "In vivo modulation of murine myelopoiesis following intravenous administration of prostaglandin E2," Blood, 62(5):1100-1107 (1983).

(56) References Cited

OTHER PUBLICATIONS

Gidali et al., "The effect of E type prostaglandins on the proliferation of haemopoietic stem cells in vivo," Cell Tissue Kinet., 10:365-373 (1977).
Goessling et al., "Genetic interaction of PGE2 and Wnt signaling regulates developmental specification of stem cells and regeneration," Cell, 136:1136-1147 (2009).
Goessling et al., "Genetic interaction of PGE2 and Wnt signaling regulates developmental specification of stem cells and regeneration," Cell, vol. 136, Supplemental Data (2009).
Goessling et al., "Prostaglandin E2 enhances human cord blood stem cell xenotransplants and shows long-term safety in preclinical nonhuman primate transplant models," Cell Stem Cell, 8(4):445-458 (2011).
Goichberg et al., "cAMP-induced PKCzeta activation increases functional CXCR4 expression on human CD34+ hematopoietic progenitors," Blood, 107(3):870-879 (2006).
Guatelli et al., "Isothermal, in vitro amplification of nucleic acids by a multienzyme reaction modeled after retroviral replication," Proc. Natl. Acad. Sci USA, 87(5):1874-1878 (1990).
Hanson et al., "16, 16-Dimethyl prostaglandin e2 induces radioprotection in murine intestinal and hematopoietic stem cells," Radiat. Res., 103:196-203 (1985).
Herrler et al., Prostaglandin E positively modulates endothelial progenitor cell homeostasis: an advanced treatment modality for autologous cell therapy, J. Vasc. Res., 46:333-346 (2009).
Hoggatt et al., "Eicosanoid regulation of hematopoiesis and hematopoietic stem and progenitor trafficking," Leukemia, 24(12):1993-2002 (2010).
Hoggatt et al., "Prostaglandin E2 enhances hematopoietic stem cell homing, survival, and proliferation," Blood, 113(22):5444-5455 (2009).
Horowitz, "Uses and Growth of Hematopoietic Cell Transplantation," In: Blume KG, Forman SJ, Appelbaum FR, eds. Thomas' Hematopoietic Cell Transplantation, 3rd ed. Malden, Mass: Blackwell, pp. 9-15 (2007).
Hsia and Zon, "Transcriptional regulation of hematopoietic stem cell development in zebrafish," Exp. Hematol., 33:1007-1014 (2005).
Hubbell et al., Principles of Tissue Engineering, 2nd Ed, Academic Press, San Diego, CA, pp. 237-250 (2000).
Ito et al., "Clinical application of hematopoietic stem cell transplantation," J. Clin. Exp. Med., 229(9):786-792 (2009), English abstract attached.
Jandl, Blood: Textbook of Hematology, 2nd Ed., Little, Brown and Company, Boston, MA pp. 544-545 (1996).
Janssens et al., "The Wnt-dependent signaling pathways as target in oncology drug discovery," Invest. New Drugs, 24:263-280 (2006).
Kahn et al., "Overexpression of CXCR4 on human CD34+ progenitors increases their proliferation, migration, and NOD/SCID repopulation," Blood, 103(8):2942-2949 (2004).
Kamel et al., "Potential interaction of prostaglandin and Wnt signaling pathways mediating bone cell responses to fluid flow," J. Bone and Mineral Res., vol. 21, NR, Suppl. 1, p. S92, (2006).
Kataoka et al., "Prostaglandin E2 receptor EP4 agonist induces Bcl-xL and independently activates proliferation signals in mouse primary hepatocytes," J. Gastroenterology, 40(6):610-616 (2005).
Kishi et al., "Bone marrow suppression induced by high dose valproic acid," Arch. Dis. Child., 71(2):153-155 (1994).
Kollet et al., "Human CD34+CXCR4-sorted cells harbor intracellular CXCR4, which can be functionally expressed and provide NOD/SCID repopulation," Blood, 100(8):2778-2786 (2002).
Konturek et al., "Prostaglandins and ulcer healing," J. Physiology Pharmacology 56 (Supp 5):5-31 (2005).
Kouchoukos et al., "Elective hypothermic cardiopulmonary bypass and circulatory arrest for spinal cord protection during operations on the thoracoabdominal aorta," J. Thorac. Cardiovasc. Surg., 99:659-664 (1990).
Krishnan et al., "Regulation of bone mass by Wnt signaling," J. Clin. Invest., 116(5):1202-1209(2006).
Kurtzberg et al., "Unrelated placental blood in marrow transplantation," Stem Cells 18:153-154 (2000).
Kwoh et al., "Transcription-based amplification system and detection of amplified human immunodeficiency virus type 1 with a bead-based sandwich hybridization format," Proc. Natl. Acad. Sci USA, 86(4):1173-1177 (1989).
Kyriakou et al., "Factors that influence short-term homing of human bone marrow-derived mesenchymal stem cells in a xenogeneic animal model," Haematologica—The Hematology Journal 93(10):1457-1465 (2008).
Lee et al., "Mechanisms involved in prostaglandin E2-mediated neuroprotection against TNF-alpha: possible involvement of multiple signal transduction and beta-catenin/T-Cell factor," J. Neuroimmunol., 155(1-2):21-31 (2004).
Liu et al., "Ex vivo expansion of hematopoietic stem cells derived from umbilical cord blood in rotating wall vessel," J. Biotechnol., 124:592-601 (2006).
Lizardi et al., "Exponential amplification of recombinant-RNA hybridization probes," Bio/Technology, 6:1197-1202 (1988).
McCowage et al., "Multiparameter-fluorescence activated cell sorting analysis of retroviral vector gene transfer into primitive umbilical cord blood cells," Exp. Hematol., 26(4):288-298 (1998).
North and Zon, "Modeling human hematopoietic and cardiovascular diseases in zebrafish," Dev. Dyn., 228:568-583 (2003).
North et al., "Prostaglandin E2 regulates vertebrate haematopoietic stem cell homeostasis," Nature, 447:1007-1011 (2007).
Okamoto et al., "Molecular and clinical basis for the regeneration of human gastrointestinal epithelia," J. Gastroenterol, 39:1-6 (2004).
Okunieff et al., "Effects of hydralazine on in vivo tumor energy metabolism, hematopoietic radiation sensitivity, and cardiovascular parameters," Int. J. Radiat. Oncol. Biol. Phys., 16(5):1145-1148 (1989).
Pachence et al., Principles of Tissue Engineering, 2nd Ed, Academic Press, San Diego, CA pp. 263-277 (2000).
Paladin Labs Inc., "Summary basis of decision (SBD) PRVANTAS®, Histrelin acetate subdermal implant, 50mg," Submission Control No. 092567, 24 pages. (2006).
Pelus et al., "Pleiotropic effects of prostaglandin $E_2$ in hematopoiesis; prostaglandin $E_2$ and other eicosanoids regulate hematopoietic stem and progenitor cell function," Prostaglandins & other Lipid Mediators, 96:3-9 (2011).
Quackenbush, "Microarray data normalization and transformation," Nat. Genet., 32(Suppl):496-501 (2002).
SAFC Biosciences, Technical Bulletin, BIOEZE™ Bags—polyethylene (PE) film, 4 pages (2006).
Saltzman et al., Principles of Tissue Engineering, 2nd Ed, Academic Press, San Diego, CA pp. 221-235 (2000).
Sankaranarayanan et al., "Radioprotective Effects of Prostaglandins for Chromosomal Aberrations and Cell Killing in V79 Chinese Hamster Cells Grown as Spheroids in Vitro and for Mouse Spermatogonial Stem Cells and Bone Marrow Cells in Vivo," Int. J. Radiation Biol., 67(1):47-55 (1995).
Schena et al., "Quantitative monitoring of gene expression patterns with a complementary DNA microarray," Science, 270(5235):467-470 (1995).
Schmidt et al., "Influence of prostaglandin on repair of rat stomach damaged by absolute ethanol," J. Surg. Res., 41(4):367-377 (1986).
Shao et al., "Prostaglandin E2 induces VEGF expression via the Wnt pathway," Gastroenterology, vol. 128, NR. 4, Suppl. 2, p. A146 (2005).
Shevtsov et al., "Activation of beta-catenin signaling pathways by classical G-protein-coupled receptors: mechanisms and consequences in cycling and non-cycling cells," Cell Cycle, 5(20):2295-2300(2006) Epub Oct. 16, 2006.
Shi et al., "Regulation of CXCR4 expression in human mesenchymal stem cells by cytokine treatment: role in homing efficiency in NOD/SCID mice," Haematologica—The Hematology Journal 92(7):897-904 (2007).
Stier et al., "Notch1 activation increases hematopoietic stem cell self-renewal in vivo and favors lymphoid over myeloid lineage outcome," Blood, 99(7):2369-78 (2002).

(56) References Cited

OTHER PUBLICATIONS

Takayama et al., Principles of Tissue Engineering, 2nd Ed, Academic Press, San Diego, CA pp. 209-220 (2000).

Thomson et al., Principles of Tissue Engineering, 2nd Ed, Academic Press, San Diego, CA pp. 251-262 (2000).

Tocris Bioscience, Safety Data Sheet. Product Name: Prostaglandin E2. Catalog No. 2296. CAS No. 363-24-6, Version 2.0 SDS Revision Date: Dec. 19, 2008, SDS Print Date Jan. 22, 2014, four pages.

Tseng Al-Sun et al., "The GSK-3 inhibitor BIO promotes proliferation in mammalian,".Chem. Biol., 13:957-963 (2006).

Urakawa et al., "Study of 16, 16-dimethyl prostaglandin E2 for prevention of stress ulcer after hepatectomy of experimental cirrhotic liver and its influence on hepatic regeneration," Database EMBASE [online] 1990.

Wagner et al., "Transplantation of unrelated donor umbilical cord blood in 102 patients with malignant and nonmalignant diseases: influence of CD34 cell dose and HLA disparity on treatment-related mortality and survival," Blood, 100(5):1611-1618 (2002).

Walden, TL Jr. et al., Abstract only. "16,16-Dimethyl prostaglandin E2 increases survival in mice following irradiation," Radial. Res., 109(3):440-448 (1987).

Weis et al., "Detection of rare mRNAs via quantitative RT-PCT," Trends Genet., 8(8):263-264 (1992).

WHO Pharmacopoeia Library, "Methods of analysis: 1. physical and physiochemical methods: 1.14 chromatography: 1.14.4 high-performance liquid chromatography," Retrieved from internet. http://apps.who.int/phint/en/p/docf/, Aug. 15, 2003.

Wu et al., "Extracellular calcium increases CXCR4 expression on bone marrow-derived cells and enhances pro-angiogenesis therapy," J. Cell. Mol. Med., 13(9B):3764-3773 (2009).

Affymetrix, "Data Sheet. GeneChip® Human Genome U133 Arrays. the most comprehensive coverage of the human genome in two flexible formats: single-array cartridges and multi-array plates," Affymetrix (2007).

Pelus et al., "Pulse exposure of haematopoietic grafts to prostaglandin $E_2$ in vitro facilitates engraftment and recovery," Cell Prolif., 44(Suppl. 1):22-29 (2011).

\* cited by examiner

CELL POTENCY ASSAY FOR THERAPEUTIC POTENTIAL

CROSS-REFERENCE TO RELATED APPLICATIONS

This application claims the benefit under 35 U.S.C. § 119(e) of U.S. Provisional Application No. 61/789,717, filed Mar. 15, 2013, which is incorporated by reference in its entirety.

BACKGROUND

Technical Field

The invention generally relates to assays and methods used to measure, identify, determine, confirm, and/or validate the therapeutic potential of cell therapy products. More particularly, the invention relates to cell potency assays used to confirm, and/or validate the therapeutic potential of hematopoietic cell compositions, and use thereof, including use for increasing hematopoietic cell engraftment, reconstitution, homing, and/or proliferation in vivo.

Description of the Related Art

The goal of regenerative medicine is to maintain, improve or even restore the function of damaged or diseased cells, tissues, and organs. One way that regenerative medicine aims to revolutionize the practice of medicine is to employ cell-based therapeutics to treat patients. However, for the promise of cell-based therapeutics to be fully realized, the therapeutic cells should not only be well-tolerated when introduced into a patient, but the cells should also have the requisite level of therapeutic potential needed to provide a benefit to the patient.

An important aspect of evaluating cell-based products is potency testing. Cell potency assays involve the quantitative measure of biological activity of a cell-based product. The biological activity should describe the ability of a cell-based product to achieve a defined biological effect. The biological activity measured should be closely related to the cell-based product's intended biological effect and ideally, it should be related to the cell-based product's clinical purpose. Measurement of the potency of a cell-based product is not the same as measuring clinical efficacy. Rather, it is a means to control product quality and provide appropriate release criteria. Potency assays for cell-based products usually take a considerable amount of time to develop.

One emerging area of regenerative medicine is stem and progenitor cell transplants, e.g., bone marrow, umbilical cord blood, mobilized peripheral blood, and hematopoietic stem cell transplants, used to treat various genetic diseases, cancers, and degenerative disorders. However, the current state of cell potency assays for validating the therapeutic potential of cell-based transplant therapies is expensive, time-consuming, inefficient, and unreliable. Moreover, there is no uniform framework for a cell potency assay that could be adapted across different clinical transplant platforms.

SUMMARY OF THE INVENTION

The invention generally provides novel cell potency assays to measure, identify, determine, and/or validate the therapeutic potential of cell populations and related uses thereof.

In various embodiments, a method is provided to measure the therapeutic potential of hematopoietic cells comprising: a) measuring expression of a plurality of genes in a population of cells comprising hematopoietic cells; b) calculating a score for the expression measured for the plurality of genes, wherein the score indicates the therapeutic potential of the hematopoietic cells; c) comparing the score to a pre-determined cut-off; wherein the hematopoietic cells have sufficient therapeutic potential if the score is above a pre-determined cut-off; or wherein the hematopoietic cells do not have sufficient therapeutic potential if the score is below the pre-determined cut-off.

In one embodiment, the population of cells is bone marrow cells (BMCs), umbilical cord blood cells (UCBCs), placental blood cells, mobilized peripheral blood cells (MPBCs), hematopoietic stem cells (HSCs), hematopoietic progenitor cells (HPCs), or CD34+ cells.

In a particular embodiment, the population of hematopoietic cells is isolated from bone marrow, umbilical cord blood, placental blood, or mobilized peripheral blood.

In a certain embodiment, at least a portion of the hematopoietic cells is modulated ex vivo prior to measuring expression of the plurality of genes.

In a further embodiment, at least a portion of the hematopoietic cells is expanded ex vivo prior to measuring expression of the plurality of genes.

In a particular embodiment, at least a portion of the hematopoietic cells is cryopreserved prior to measuring expression of the plurality of genes.

In an additional embodiment, at least a portion of the hematopoietic cells comprises a genetic modification.

In another embodiment, the genetically modified cells are suitable for gene therapy.

In one embodiment, the hematopoietic cells are modulated ex vivo prior to measuring expression of the plurality of genes by contacting the population of hematopoietic cells with at least one agent selected from the group consisting of a cAMP analogue or enhancer, a Ga-s activator, and a prostaglandin pathway agonist.

In a particular embodiment, the prostaglandin pathway agonist selectively binds the PGE2 EP2 or PGE2 EP4 receptor.

In a certain embodiment, the prostaglandin pathway agonist comprises PGE2, or a PGE2 analogue or derivative.

In an additional embodiment, the prostaglandin pathway agonist is selected from the group consisting of: PGE2, 16,16-dmPGE2, 15(S)-15-methyl PGE2, 20-ethyl PGE2, and 8-iso-16-cyclohexyl-tetranor PGE2.

In another embodiment, the prostaglandin pathway agonist comprises 16,16-dmPGE2.

In yet another embodiment, the hematopoietic cells is further contacted with a glucocorticoid.

In one embodiment, the hematopoietic cells have been contacted with the at least one agent for a time of at least about one hour.

In a particular embodiment, the hematopoietic cells have been contacted with the at least one agent for a time of at least about two hours.

In a further embodiment, the hematopoietic cells have been contacted with the at least one agent for a time of at least about four hours.

In an additional embodiment, the hematopoietic cells have been contacted with the at least one agent for a time of at least about six hours.

In a further embodiment, the hematopoietic cells have been contacted with the at least one agent for a time of at least 12 hours.

In a particular embodiment, the hematopoietic cells have been contacted with the at least one agent for a time of at least about 24 hours.

In one embodiment, the hematopoietic cells have been contacted with the at least one agent for a time of at least about one hour to at least about 24 hours.

In another embodiment, the hematopoietic cells have been contacted with the at least one agent for a time of at least about one hour to at least about 12 hours.

In a certain embodiment, the hematopoietic cells have been contacted with the at least one agent for a time of at least about one hour to at least about six hours.

In one embodiment, hematopoietic cells have been contacted with the at least one agent for a time of at least about one hour to at least about four hours.

In another embodiment, the hematopoietic cells have been contacted with the at least one agent for a time of at least about one hour to at least about two hours.

In a particular embodiment, the hematopoietic cells have been contacted with the at least one agent at a temperature of about 37° C.

In a further embodiment, the hematopoietic cells have been contacted with the at least one agent at a temperature of about 30° C.

In an additional embodiment, wherein the hematopoietic cells have been contacted with the at least one agent at a temperature of about 25° C.

In a certain embodiment, the hematopoietic cells have been contacted with the at least one agent at a temperature of about 25° C. to about 37° C.

In a particular embodiment, the hematopoietic cells have been contacted with the at least one agent at a temperature of about 30° C. to about 37° C.

In one embodiment, the plurality of genes comprises two or more genes selected from the group consisting of: hairy/enhancer-of-split related with YRPW motif 1 (HEY1), UL16 binding protein 2 (ULBP2), hyaluronan synthase 1 (HAS1), GTP-binding protein GEM (GEM), renin (REN), collagen, type I, alpha 1 (COL1A1), cyclooxygenase 2 (COX-2), angiopoietin 1 (ANGPT1), chemokine (C-X-C motif) ligand 6 (CXCL6), prominin 1 (PROM1), bone morphogenetic protein 4 (BMP4), angiopoietin 2 (ANGPT2), inhibitor of kappaB kinase beta (IKBKB), platelet/endothelial cell adhesion molecule 1 (PECAM1), tyrosine kinase with immunoglobulin-like and EGF-like domains 1 (TIE1), amphiregulin (AREG), caspase 3 (CASP3), jagged 1 (JAG1), aryl hydrocarbon receptor nuclear translocator (ARNT), cAMP-responsive element modulator (CREM), connective tissue growth factor (CTGF), CD40 ligand (CD40L), BCL2-associated X protein (BAX), hepatocyte growth factor (HGF), superoxide dismutase 2 (SOD2), platelet derived growth factor B (PDGFB), thrombospondin 1 (THBS1), dual specificity protein phosphatase 4 (DUSP4), cysteine-rich protein 61 (CYR61), chemokine (C-X-C motif) ligand 1 (CXCL1), endothelial tyrosine kinase (TEK), CASP8 and FADD-like apoptosis regulator (CFLAR), insulin growth factor 2 (IGF2), chemokine (C-X-C motif) receptor 4 (CXCR4), matrix metalloprotease 2 (MMP2), fibroblast growth factor 2 (FGF2), prostaglandin-endoperoxide synthase 2 (PTGS2), RAS-related C3 botulinum substrate 2 (RAC2), platelet derived growth factor receptor (PDGFR), nuclear receptor subfamily 4, group A, member 2 (NR4A2), nuclear receptor subfamily 4, group A, member 3 (NR4A3), telomerase reverse transcriptase (TERT), transforming growth factor beta 1 (TGFB1), matrix metalloprotease 9 (MMP9), CD40 antigen (CD40), CD44 antigen (CD44), high mobility group box 1 (HMGB1), nitrogen oxide synthase 3 (NOS3), kinase insert domain receptor (KDR), integrin beta 1 (ITGB1), catenin (cadherin-associated protein), beta 1 (CTNNB1), colony stimulating factor 3 (CSF3), interleukin 8 (IL8), plasminogen activator, urokinase receptor (PLAUR), B-cell CLL/lymphoma 2 (BCL2), bone morphogenetic protein 2 (BMP2), colony stimulating factor 1 (CSF1), v-akt murine thymoma viral oncogene homolog 1 (AKT1), vascular endothelial growth factor A (VEGFA), intercellular adhesion molecule 1 (ICAM1), chemokine (C-X-C motif) ligand 3 (CXCL3), caspase 8 (CASP8), CD34 antigen (CD34), interleukin 1A (IL1A), CD47 antigen (CD47), chemokine (C-C motif) ligand 7 (CCL7), hypoxia inducible factor 1A (HIF1A), EDN1 (endothelin 1), sphingosine-1-phosphate receptor 1 (S1PR1), chemokine (C-C motif) receptor 1 (CCR1), SMAD family member 4 (SMAD4), fms-related tyrosine kinase 1 (FLT1), CD151 antigen (CD151), placental growth factor (PGF), nuclear factor of kappa light polypeptide gene enhancer in B-cells 1 (NFKB1), SMAD family member 2 (SMAD2), CXC chemokine receptor 7 (CXCR7), transforming growth factor beta 3 (TGFB3), chemokine (C-X-C motif) ligand 5 (CXCL5), cyclin D1 (CCND1), heparin-binding EGF-like growth factor (HBEGF), nuclear receptor subfamily 3, group C, member 1 (NR3C1), tumor necrosis factor (TNF), integrin alpha L (ITGAL), CXC chemokine receptor 2 (CXCR2), signal transducer and activator of transcription 1 (STAT1), integrin alpha 4 (ITGA4), leukemia inhibitory factor (LIF), RAS p21 protein activator 1 (RASA1), cadherin 5 (CDH5), ephrin B2 (EFNB2), regulator of G-protein signaling 16 (RGS16), chemokine (C-X-C motif) ligand 2 (CXCL2), integrin alpha 5 (ITGA5), chemokine (C-X-C motif) ligand 12 (CXCL12), tissue inhibitor of metalloprotease 1 (TIMP1), Fos-related antigen 2 (FOSL2), integrin beta 2 (ITGB2), and tissue inhibitor of metalloprotease 2 (TIMP2).

In another embodiment, the plurality of genes comprises five or more of the genes selected from the group consisting of: HEY1, COX2, ULBP2, HAS1, GEM1, REN, COL1A1, ANGPT1, CXCL6, PROM1, BMP4, ANGPT2, IKBKB, PECAM1, TIE1, AREG, CASP3, JAG1, ARNT, CREM, CTGF, CD40L, BAX, HGF, SOD2, PDGFB, THBS1, DUSP4, CYR61, CXCL1, TEK, CFLAR, IGF2, CXCR4, MMP2, FGF2, PTGS2, RAC2, PDGFR, NR4A2, NR4A3, TERT, TGFB1, MMP9, CD40, CD44, HMGB1, NOS3, KDR, ITGB1, CTNNB1, CSF3, IL8, PLAUR, BCL2, BMP2, CSF1, AKT1, VEGFA, ICAM1, CXCL3, CASP8, CD34, IL1A, CD47, CCL7, HIF1A, EDN1, S1PR1, CCR1, SMAD4, FLT1, CD151, PGF, NFKB1, SMAD2, CXCR7, TGFB3, CXCL5, CCND1, HBEGF, NR3C1, TNF, ITGAL, CXCR2, STAT1, ITGA4, LIF, RASA1, CDH5, EFNB2, RGS16, CXCL2, ITGA5, CXCL12, TIMP1, FOSL2, ITGB2, and TIMP2.

In a particular embodiment, the plurality of genes comprises five or more of the genes selected from the group consisting of: HEY1, COX2, ULBP2, HAS1, GEM1, REN, COL1A1, ANGPT1, CXCL6, PROM1, BMP4, ANGPT2, IKBKB, PECAM1, TIE1, AREG, CASP3, JAG1, ARNT, CREM, CTGF, CD40L, BAX, HGF, SOD2, PDGFB, THBS1, DUSP4, CYR61, CXCL1, TEK, CFLAR, IGF2, CXCR4, MMP2, FGF2, PTGS2, RAC2, PDGFR, NR4A2, NR4A3, TERT, TGFB1, MMP9, CD40, CD44, HMGB1, NOS3, KDR, ITGB1, CTNNB1, CSF3, IL8, PLAUR, BCL2, BMP2, CSF1, AKT1, VEGFA, ICAM1, CXCL3, CASP8, CD34, IL1A, CD47, CCL7, HIF1A, EDN1, S1PR1, CCR1, SMAD4, FLT1, CD151, PGF, NFKB1, SMAD2, CXCR7, TGFB3, CXCL5, CCND1, HBEGF, NR3C1, TNF, ITGAL, CXCR2, STAT1, ITGA4, LIF, RASA1, CDH5, EFNB2, RGS16, CXCL2, ITGA5, CXCL12, TIMP1, FOSL2, ITGB2, and TIMP2.

In an additional embodiment, the plurality of genes comprises two or more genes selected from the group consisting of: CREM, GEM, NR4A2, NR4A3, IL1A, COX2, HEY1, HAS1, CXCL2, CXCL3, ULBP2, and CXCR4.

In a further embodiment, the plurality of genes comprises: CREM, GEM, NR4A2, NR4A3, IL1A, COX2, HEY1, CXCL2, CXCL3, and ULBP2.

In an additional embodiment, the plurality of genes comprises two or more genes selected from the group consisting of: CREM, GEM, NR4A2, NR4A3, IL1A, COX2, HAS1, HAS1, CXCL2, CXCL3, and CXCR4.

In a further embodiment, the plurality of genes comprises: CREM, GEM, NR4A2, NR4A3, IL1A, COX2, HAS1, CXCL2, CXCL3, and CXCR4.

In one embodiment, expression of at least two of the plurality of genes is increased in the by about 20-fold compared to expression of the at least two of the plurality of genes in a control population of hematopoietic cells.

In a certain embodiment, expression of at least five of the plurality of genes is increased by about 10-fold compared to expression of the at least two of the plurality of genes in a control population of hematopoietic cells.

In another embodiment, expression of at least five of the plurality of genes is increased by about 3-fold compared to expression of the at least two of the plurality of genes in a control population of hematopoietic cells.

In one embodiment, wherein expression of at least five of the plurality of genes is increased by about 2-fold compared to expression of the at least two of the plurality of genes in a control population of hematopoietic cells.

In another embodiment, expression of at least ten of the plurality of genes is increased by about 3-fold compared to expression of the at least two of the plurality of genes in a control population of hematopoietic cells.

In a particular embodiment, expression of at least ten of the plurality of genes is increased by about 2-fold compared to expression of the at least two of the plurality of genes in a control population of hematopoietic cells.

In another embodiment, the hematopoietic cells is contacted with 10 μM 16,16-dmPGE2, at about 37° C., for about two hours.

In an additional embodiment, the hematopoietic cells having sufficient therapeutic potential is administered to a subject in need thereof.

In a certain embodiment, the subject in need has a disease, disorder, or condition selected from the group consisting of: ischemia, a non malignant blood disorder, an immunodeficiency, severe combined immunodeficiency (SCID), lymphocytopenia, thrombocytopenia, neutropenia, anemia, Fanconi's anemia, severe aplastic anemia, a congenital hemoglobinopathy, sickle cell disease, β-thalassemaia, sickle-cell disease, Wiskott-Aldrich syndrome, a metabolic storage disease, Hurler's disease, Hunter's disease, mannosidosis, a cancer, a hematological malignancy, acute leukemia, chronic myeloid leukemia chronic lymphoid leukemia, Hodgkin's lymphoma, non-Hodgkin's lymphoma, multiple myeloma, myelodysplastic syndrome, a non-hematological cancer, breast cancer, ovarian cancer, brain cancer, prostate cancer, lung cancer, colon cancer, skin cancer, liver cancer, pancreatic cancer, Gaucher's disease, Krabbe's disease, metachromatic leukodystrophy, Tay-Sachs, Nieman Pick, glycoproteinoses (e.g., fucosidosis, a-mannosidosis), and MPS-III (Sanfillipo).

In a further embodiment, the population of cells is whole cord blood and the plurality of the signature genes selected from the group consisting of: CREM, GEM, NR4A2, NR4A3, IL1A, CXCL2, CXCL3, HAS1, COX2, and ULBP2.

In a particular embodiment, the population of cells is whole cord blood and the plurality of the signature genes comprises CREM, GEM, NR4A2, NR4A3, IL1A, CXCL2, CXCL3, HEY1, COX2, and ULBP2.

In one embodiment, the population of cells is isolated CD34+ cells and the plurality of the signature genes is selected from the group consisting of: CREM, GEM, NR4A2, NR4A3, CXCL2, CXCL3, HEY1, CXCR4, COX2, and ULBP2.

In another embodiment, the population of cells is isolated CD34+ cells and the plurality of the signature genes comprises CREM, GEM, NR4A2, NR4A3, CXCL2, CXCL3, HEY1, CXCR4, COX2, and ULBP2.

In various embodiments, an in vitro or ex vivo method is provided to determine the therapeutic potential of a population of cells comprising: a) measuring expression of a plurality of genes in a population of cells comprising hematopoietic cells; b) identifying increased expression in at least two of the plurality of genes in the population of cells compared to a control population of cells; wherein the hematopoietic cells have sufficient therapeutic potential if the increased expression in the at least two of the plurality of genes in the population of cells is at least two-fold.

In a certain embodiment, the population of cells is bone marrow cells (BMCs), umbilical cord blood cells (UCBCs), placental blood cells, mobilized peripheral blood cells (MPBCs), hematopoietic stem cells (HSCs), hematopoietic progenitor cells (HPCs), or CD34+ cells.

In one embodiment, the population of cells is isolated from bone marrow, umbilical cord blood, placental blood, or mobilized peripheral blood.

In another embodiment, at least a portion of the population of cells is modulated ex vivo prior to measuring expression of the plurality of genes.

In an additional embodiment, at least a portion of the population of cells is expanded ex vivo prior to measuring expression of the plurality of genes.

In a particular embodiment, at least a portion of the population of cells is cryopreserved prior to measuring expression of the plurality of genes.

In a particular embodiment, at least a portion of the population of cells comprises a genetic modification.

In another embodiment, the genetically modified cells are suitable for gene therapy.

In yet another embodiment, the population of cells is modulated ex vivo prior to measuring expression of the plurality of genes by contacting the population of cells with at least one agent selected from the group consisting of a cAMP analogue or enhancer, a Ga-s activator, and a prostaglandin pathway agonist.

In a further embodiment, the prostaglandin pathway agonist selectively binds the PGE2 EP2 or PGE2 EP4 receptor.

In another embodiment, the prostaglandin pathway agonist comprises PGE2, or a PGE2 analogue or derivative.

In another further embodiment, the prostaglandin pathway agonist is selected from the group consisting of: PGE2, 16,16-dmPGE2, 15(S)-15-methyl PGE2, 20-ethyl PGE2, and 8-iso-16-cyclohexyl-tetranor PGE2.

In a certain embodiment, the prostaglandin pathway agonist comprises 16,16-dmPGE2.

In an additional embodiment, the population of cells is further contacted with a glucocorticoid.

In an additional embodiment, the population of cells has been contacted with the at least one agent for a time of at least about one hour.

In a further embodiment, the population of cells has been contacted with the at least one agent for a time of at least about two hours.

In a particular embodiment, the population of cells has been contacted with the at least one agent for a time of at least about four hours.

In another embodiment, the population of cells has been contacted with the at least one agent for a time of at least about six hours.

In a particular embodiment, the population of cells has been contacted with the at least one agent for a time of at least about 12 hours.

In a certain embodiment, the population of cells has been contacted with the at least one agent for a time of at least about 24 hours.

In one embodiment, the population of cells has been contacted with the at least one agent for a time of at least about one hour to at least about 24 hours.

In a particular embodiment, the population of cells has been contacted with the at least one agent for a time of at least about one hour to at least about 12 hours.

In a further embodiment, the population of cells has been contacted with the at least one agent for a time of at least about one hour to at least about six hours.

In one embodiment, the population of cells has been contacted with the at least one agent for a time of at least about one hour to at least about four hours.

In another embodiment, the population of cells has been contacted with the at least one agent for a time of at least about one hour to at least about two hours.

In a further embodiment, the population of cells has been contacted with the at least one agent at a temperature of about 37° C.

In a certain embodiment, the population of cells has been contacted with the at least one agent at a temperature of about 30° C.

In an additional embodiment, the population of cells has been contacted with the at least one agent at a temperature of about 25° C.

In another embodiment, the population of cells has been contacted with the at least one agent at a temperature of about 25° C. to about 37° C.

In one embodiment, the population of cells has been contacted with the at least one agent at a temperature of about 30° C. to about 37° C.

In a certain embodiment, the plurality of genes comprises two or more genes selected from the group consisting of: hairy/enhancer-of-split related with YRPW motif 1 (HEY1), UL16 binding protein 2 (ULBP2), hyaluronan synthase 1 (HAS1), GTP-binding protein GEM (GEM), renin (REN), collagen, type I, alpha 1 (COL1A1), cyclooxygenase 2 (COX-2), angiopoietin 1 (ANGPT1), chemokine (C-X-C motif) ligand 6 (CXCL6), prominin 1 (PROM1), bone morphogenetic protein 4 (BMP4), angiopoietin 2 (ANGPT2), inhibitor of kappaB kinase beta (IKBKB), platelet/endothelial cell adhesion molecule 1 (PECAM1), tyrosine kinase with immunoglobulin-like and EGF-like domains 1 (TIE1), amphiregulin (AREG), caspase 3 (CASP3), jagged 1 (JAG1), aryl hydrocarbon receptor nuclear translocator (ARNT), cAMP-responsive element modulator (CREM), connective tissue growth factor (CTGF), CD40 ligand (CD40L), BCL2-associated X protein (BAX), hepatocyte growth factor (HGF), superoxide dismutase 2 (SOD2), platelet derived growth factor B (PDGFB), thrombospondin 1 (THBS1), dual specificity protein phosphatase 4 (DUSP4), cysteine-rich protein 61 (CYR61), chemokine (C-X-C motif) ligand 1 (CXCL1), endothelial tyrosine kinase (TEK), CASP8 and FADD-like apoptosis regulator (CFLAR), insulin growth factor 2 (IGF2), chemokine (C-X-C motif) receptor 4 (CXCR4), matrix metalloprotease 2 (MMP2), fibroblast growth factor 2 (FGF2), prostaglandin-endoperoxide synthase 2 (PTGS2), RAS-related C3 botulinum substrate 2 (RAC2), platelet derived growth factor receptor (PDGFR), nuclear receptor subfamily 4, group A, member 2 (NR4A2), nuclear receptor subfamily 4, group A, member 3 (NR4A3), telomerase reverse transcriptase (TERT), transforming growth factor beta 1 (TGFB1), matrix metalloprotease 9 (MMP9), CD40 antigen (CD40), CD44 antigen (CD44), high mobility group box 1 (HMGB1), nitrogen oxide synthase 3 (NOS3), kinase insert domain receptor (KDR), integrin beta 1 (ITGB1), catenin (cadherin-associated protein), beta 1 (CTNNB1), colony stimulating factor 3 (CSF3), interleukin 8 (IL8), plasminogen activator, urokinase receptor (PLAUR), B-cell CLL/lymphoma 2 (BCL2), bone morphogenetic protein 2 (BMP2), colony stimulating factor 1 (CSF1), v-akt murine thymoma viral oncogene homolog 1 (AKT1), vascular endothelial growth factor A (VEGFA), intercellular adhesion molecule 1 (ICAM1), chemokine (C-X-C motif) ligand 3 (CXCL3), caspase 8 (CASP8), CD34 antigen (CD34), interleukin 1A (IL1A), CD47 antigen (CD47), chemokine (C-C motif) ligand 7 (CCL7), hypoxia inducible factor 1A (HIF1A), EDN1 (endothelin 1), sphingosine-1-phosphate receptor 1 (S1PR1), chemokine (C-C motif) receptor 1 (CCR1), SMAD family member 4 (SMAD4), fms-related tyrosine kinase 1 (FLT1), CD151 antigen (CD151), placental growth factor (PGF), nuclear factor of kappa light polypeptide gene enhancer in B-cells 1 (NFKB1), SMAD family member 2 (SMAD2), CXC chemokine receptor 7 (CXCR7), transforming growth factor beta 3 (TGFB3), chemokine (C-X-C motif) ligand 5 (CXCL5), cyclin D1 (CCND1), heparin-binding EGF-like growth factor (HBEGF), nuclear receptor subfamily 3, group C, member 1 (NR3C1), tumor necrosis factor (TNF), integrin alpha L (ITGAL), CXC chemokine receptor 2 (CXCR2), signal transducer and activator of transcription 1 (STAT1), integrin alpha 4 (ITGA4), leukemia inhibitory factor (LIF), RAS p21 protein activator 1 (RASA1), cadherin 5 (CDH5), ephrin B2 (EFNB2), regulator of G-protein signaling 16 (RGS16), chemokine (C-X-C motif) ligand 2 (CXCL2), integrin alpha 5 (ITGA5), chemokine (C-X-C motif) ligand 12 (CXCL12), tissue inhibitor of metalloprotease 1 (TIMP1), Fos-related antigen 2 (FOSL2), integrin beta 2 (ITGB2), and tissue inhibitor of metalloprotease 2 (TIMP2).

In a particular embodiment, the plurality of genes comprises five or more of the genes selected from the group consisting of: HEY1, COX2, ULBP2, HAS1, GEM1, REN, COL1A1, ANGPT1, CXCL6, PROM1, BMP4, ANGPT2, IKBKB, PECAM1, TIE1, AREG, CASP3, JAG1, ARNT, CREM, CTGF, CD40L, BAX, HGF, SOD2, PDGFB, THBS1, DUSP4, CYR61, CXCL1, TEK, CFLAR, IGF2, CXCR4, MMP2, FGF2, PTGS2, RAC2, PDGFR, NR4A2, NR4A3, TERT, TGFB1, MMP9, CD40, CD44, HMGB1, NOS3, KDR, ITGB1, CTNNB1, CSF3, IL8, PLAUR, BCL2, BMP2, CSF1, AKT1, VEGFA, ICAM1, CXCL3, CASP8, CD34, IL1A, CD47, CCL7, HIF1A, EDN1, S1PR1, CCR1, SMAD4, FLT1, CD151, PGF, NFKB1, SMAD2, CXCR7, TGFB3, CXCL5, CCND1, HBEGF, NR3C1, TNF, ITGAL, CXCR2, STAT1, ITGA4, LIF, RASA1, CDH5, EFNB2, RGS16, CXCL2, ITGA5, CXCL12, TIMP1, FOSL2, ITGB2, and TIMP2.

In an additional embodiment, the plurality of genes comprises ten or more of the genes selected from the group consisting of: HEY1, COX2, ULBP2, HAS1, GEM1, REN, COL1A1, ANGPT1, CXCL6, PROM1, BMP4, ANGPT2, IKBKB, PECAM1, TIE1, AREG, CASP3, JAG1, ARNT, CREM, CTGF, CD40L, BAX, HGF, SOD2, PDGFB, THBS1, DUSP4, CYR61, CXCL1, TEK, CFLAR, IGF2, CXCR4, MMP2, FGF2, PTGS2, RAC2, PDGFR, NR4A2, NR4A3, TERT, TGFB1, MMP9, CD40, CD44, HMGB1, NOS3, KDR, ITGB1, CTNNB1, CSF3, IL8, PLAUR, BCL2, BMP2, CSF1, AKT1, VEGFA, ICAM1, CXCL3, CASP8, CD34, IL1A, CD47, CCL7, HIF1A, EDN1, S1PR1, CCR1, SMAD4, FLT1, CD151, PGF, NFKB1, SMAD2, CXCR7, TGFB3, CXCL5, CCND1, HBEGF, NR3C1, TNF, ITGAL, CXCR2, STAT1, ITGA4, LIF, RASA1, CDH5, EFNB2, RGS16, CXCL2, ITGA5, CXCL12, TIMP1, FOSL2, ITGB2, and TIMP2.

In one embodiment, the plurality of genes comprises two or more genes selected from the group consisting of: CREM, GEM, NR4A2, NR4A3, IL1A, COX2, HEY1, CXCL2, CXCL3, and ULBP2.

In a certain embodiment, the plurality of genes comprises: CREM, GEM, NR4A2, NR4A3, IL1A, HEY1, HAS1, CXCL2, CXCL3, and ULBP1.

In an additional embodiment, the plurality of genes comprises two or more genes selected from the group consisting of: CREM, GEM, NR4A2, NR4A3, IL1A, COX2, HAS1, HAS1, CXCL2, CXCL3, and CXCR4.

In a further embodiment, the plurality of genes comprises: CREM, GEM, NR4A2, NR4A3, IL1A, COX2, HAS1, CXCL2, CXCL3, and CXCR4.

In one embodiment, population of cells is whole cord blood and the plurality of the signature genes selected from the group consisting of: CREM, GEM, NR4A2, NR4A3, ILIA, CXCL2, CXCL3, HAS1, COX2, and ULBP2.

In another embodiment, the population of cells is whole cord blood and the plurality of the signature genes comprises CREM, GEM, NR4A2, NR4A3, IL1A, CXCL2, CXCL3, HEY1, COX2, and ULBP2.

In a particular embodiment, the population of cells is isolated CD34+ cells and the plurality of the signature genes is selected from the group consisting of: CREM, GEM, NR4A2, NR4A3, CXCL2, CXCL3, HEY1, CXCR4, COX2, and ULBP2.

In a further embodiment, the population of cells is isolated CD34+ cells and the plurality of the signature genes comprises CREM, GEM, NR4A2, NR4A3, CXCL2, CXCL3, HEY1, CXCR4, COX2, and ULBP2.

In another embodiment, expression of at least two of the plurality of genes is increased by about 20-fold compared to expression of the at least two of the plurality of genes in a control population of cells.

In a particular embodiment, expression of at least five of the plurality of genes is increased by about 10-fold compared to expression of the at least two of the plurality of genes in a control population of cells.

In a certain particular embodiment, expression of at least five of the plurality of genes is increased by about 3-fold compared to expression of the at least two of the plurality of genes in a control population of cells.

In an additional embodiment, expression of at least five of the plurality of genes is increased by about 2-fold compared to expression of the at least two of the plurality of genes in a control population of cells.

In a certain embodiment, expression of at least ten of the plurality of genes is increased by about 3-fold compared to expression of the at least two of the plurality of genes in a control population of cells.

In a certain embodiment, expression of at least ten of the plurality of genes is increased by about 2-fold compared to expression of the at least two of the plurality of genes in a control population of cells.

In a further embodiment, the population of cells is contacted with 10 µM, 16,16-dmPGE2, at about 37° C., for about two hours.

In another embodiment, the population of cells having sufficient therapeutic potential is administered to a subject in need thereof.

In yet another embodiment, the subject in need has a disease, disorder, or condition selected from the group consisting of: ischemia, a non malignant blood disorder, an immunodeficiency, severe combined immunodeficiency (SCID), lymphocytopenia, thrombocytopenia, neutropenia, anemia, Fanconi's anemia, severe aplastic anemia, a congenital hemoglobinopathy, sickle cell disease, β-thalassemaia, sickle-cell disease, Wiskott-Aldrich syndrome, a metabolic storage disease, Hurler's disease, Hunter's disease, mannosidosis, a cancer, a hematological malignancy, acute leukemia, chronic myeloid leukemia chronic lymphoid leukemia, Hodgkin's lymphoma, non-Hodgkin's lymphoma, multiple myeloma, myelodysplastic syndrome, a non-hematological cancer, breast cancer, ovarian cancer, brain cancer, prostate cancer, lung cancer, colon cancer, skin cancer, liver cancer, pancreatic cancer, Gaucher's disease, Krabbe's disease, metachromatic leukodystrophy, Tay-Sachs, Nieman Pick, glycoproteinoses (e.g., fucosidosis, a-mannosidosis), and MPS-III (Sanfillipo).

In various embodiments, a method is provided for increasing hematopoietic reconstitution in a subject, comprising administering a population of hematopoietic cells having sufficient therapeutic potential according to any one of the foregoing embodiments to increase hematopoietic reconstitution in the subject.

In one embodiment, the hematopoietic reconstitution is increased about 10% by hematopoeitic cells that have therapeutic potential compared to the reconstitution associated with control hematopoietic cells.

In a particular embodiment, the hematopoietic reconstitution is increased about 20% by hematopoeitic cells that have therapeutic potential compared to the reconstitution associated with control hematopoietic cells.

In another embodiment, the hematopoietic reconstitution is increased about 30% by hematopoeitic cells that have therapeutic potential compared to the reconstitution associated with control hematopoietic cells.

In a particular embodiment, the hematopoietic reconstitution is increased about 40% by hematopoeitic cells that have therapeutic potential compared to the reconstitution associated with control hematopoietic cells.

In an additional embodiment, the hematopoietic reconstitution is increased about 50% by hematopoeitic cells that have therapeutic potential compared to the reconstitution associated with control hematopoietic cells.

In a certain embodiment, the hematopoietic reconstitution is increased about two-fold by hematopoeitic cells that have therapeutic potential compared to the reconstitution associated with control hematopoietic cells.

In a further embodiment, the hematopoietic reconstitution is increased about three-fold by hematopoeitic cells that have therapeutic potential compared to the reconstitution associated with control hematopoietic cells.

In one embodiment, the hematopoietic reconstitution is increased about five-fold by hematopoeitic cells that have therapeutic potential compared to the reconstitution associated with control hematopoietic cells.

In various embodiments, a method is provided for increasing hematopoietic engraftment in a subject, comprising administering a population of hematopoietic cells having sufficient therapeutic potential according to any one of the foregoing embodiments to increase hematopoietic engraftment in the subject.

In various embodiments, a method is provided for increasing hematopoietic engraftment in a subject, comprising administering a population of hematopoietic cells having sufficient therapeutic potential according to any one of the foregoing embodiments to increase hematopoietic engraftment in the subject.

In a further embodiment, the hematopoietic engraftment is increased about 10% by hematopoeitic cells that have therapeutic potential compared to the engraftment associated with control hematopoietic cells.

In a particular embodiment, the hematopoietic engraftment is increased about 20% by hematopoeitic cells that have therapeutic potential compared to the engraftment associated with control hematopoietic cells.

In a certain embodiment, the hematopoietic engraftment is increased about 30% by hematopoeitic cells that have therapeutic potential compared to the engraftment associated with control hematopoietic cells.

In one embodiment, the hematopoietic engraftment is increased about 40% by hematopoeitic cells that have therapeutic potential compared to the engraftment associated with control hematopoietic cells.

In a particular embodiment, the hematopoietic engraftment is increased about 50% by hematopoeitic cells that have therapeutic potential compared to the engraftment associated with control hematopoietic cells.

In another embodiment, the hematopoietic engraftment is increased about two-fold by hematopoeitic cells that have therapeutic potential compared to the engraftment associated with control hematopoietic cells.

In a further embodiment, the hematopoietic engraftment is increased about three-fold by hematopoeitic cells that have therapeutic potential compared to the engraftment associated with control hematopoietic cells.

In a particular embodiment, the hematopoietic engraftment is increased about five-fold by hematopoeitic cells that have therapeutic potential compared to the engraftment associated with control hematopoietic cells.

In various embodiments, a method is provided for cell-based therapy, comprising administering a population of autologous hematopoietic cells having sufficient therapeutic potential according to any one of the foregoing embodiments to a subject in need thereof.

In various embodiments, a composition comprising a population of hematopoietic cells having therapeutic potential according to any one of the foregoing embodiments is provided.

In various embodiments, a gene expression panel is provided for identifying a population of hematopoietic cells having therapeutic potential, comprising a plurality of genes selected from the group consisting of: HEY1, COX2, ULBP2, HAS1, GEM1, REN, COL1A1, ANGPT1, CXCL6, PROM1, BMP4, ANGPT2, IKBKB, PECAM1, TIE1, AREG, CASP3, JAG1, ARNT, CREM, CTGF, CD40L, BAX, HGF, SOD2, PDGFB, THBS1, DUSP4, CYR61, CXCL1, TEK, CFLAR, IGF2, CXCR4, MMP2, FGF2, PTGS2, RAC2, PDGFR, NR4A2, NR4A3, TERT, TGFB1, MMP9, CD40, CD44, HMGB1, NOS3, KDR, ITGB1, CTNNB1, CSF3, IL8, PLAUR, BCL2, BMP2, CSF1, AKT1, VEGFA, ICAM1, CXCL3, CASP8, CD34, IL1A, CD47, CCL7, HIF1A, EDN1, S1PR1, CCR1, SMAD4, FLT1, CD151, PGF, NFKB1, SMAD2, CXCR7, TGFB3, CXCL5, CCND1, HBEGF, NR3C1, TNF, ITGAL, CXCR2, STAT1, ITGA4, LIF, RASA1, CDH5, EFNB2, RGS16, CXCL2, ITGA5, CXCL12, TIMP1, FOSL2, ITGB2, and TIMP2.

In various embodiments, a gene expression panel is provided for identifying a population of hematopoietic cells having therapeutic potential, comprising five or more genes selected from the group consisting of: HEY1, COX2, ULBP2, HAS1, GEM1, REN, COL1A1, ANGPT1, CXCL6, PROM1, BMP4, ANGPT2, IKBKB, PECAM1, TIE1, AREG, CASP3, JAG1, ARNT, CREM, CTGF, CD40L, BAX, HGF, SOD2, PDGFB, THBS1, DUSP4, CYR61, CXCL1, TEK, CFLAR, IGF2, CXCR4, MMP2, FGF2, PTGS2, RAC2, PDGFR, NR4A2, NR4A3, TERT, TGFB1, MMP9, CD40, CD44, HMGB1, NOS3, KDR, ITGB1, CTNNB1, CSF3, IL8, PLAUR, BCL2, BMP2, CSF1, AKT1, VEGFA, ICAM1, CXCL3, CASP8, CD34, IL1A, CD47, CCL7, HIF1A, EDN1, S1PR1, CCR1, SMAD4, FLT1, CD151, PGF, NFKB1, SMAD2, CXCR7, TGFB3, CXCL5, CCND1, HBEGF, NR3C1, TNF, ITGAL, CXCR2, STAT1, ITGA4, LIF, RASA1, CDH5, EFNB2, RGS16, CXCL2, ITGA5, CXCL12, TIMP1, FOSL2, ITGB2, and TIMP2.

In various embodiments, a gene expression panel is provided for identifying a population of hematopoietic cells having therapeutic potential, comprising ten or more genes selected from the group consisting of: HEY1, COX2, ULBP2, HAS1, GEM1, REN, COL1A1, ANGPT1, CXCL6, PROM1, BMP4, ANGPT2, IKBKB, PECAM1, TIE1, AREG, CASP3, JAG1, ARNT, CREM, CTGF, CD40L, BAX, HGF, SOD2, PDGFB, THBS1, DUSP4, CYR61, CXCL1, TEK, CFLAR, IGF2, CXCR4, MMP2, FGF2, PTGS2, RAC2, PDGFR, NR4A2, NR4A3, TERT, TGFB1, MMP9, CD40, CD44, HMGB1, NOS3, KDR, ITGB1, CTNNB1, CSF3, IL8, PLAUR, BCL2, BMP2, CSF1, AKT1, VEGFA, ICAM1, CXCL3, CASP8, CD34, IL1A, CD47, CCL7, HIF1A, EDN1, S1PR1, CCR1, SMAD4, FLT1, CD151, PGF, NFKB1, SMAD2, CXCR7, TGFB3, CXCL5, CCND1, HBEGF, NR3C1, TNF, ITGAL, CXCR2, STAT1, ITGA4, LIF, RASA1, CDH5, EFNB2, RGS16, CXCL2, ITGA5, CXCL12, TIMP1, FOSL2, ITGB2, and TIMP2.

In various embodiments, a gene expression panel is provided for identifying a population of hematopoietic cells having therapeutic potential, comprising the following genes: HEY1, COX2, ULBP2, HAS1, GEM1, REN, COL1A1, ANGPT1, CXCL6, PROM1, BMP4, ANGPT2, IKBKB, PECAM1, TIE1, AREG, CASP3, JAG1, ARNT, CREM, CTGF, CD40L, BAX, HGF, SOD2, PDGFB, THBS1, DUSP4, CYR61, CXCL1, TEK, CFLAR, IGF2, CXCR4, MMP2, FGF2, PTGS2, RAC2, PDGFR, NR4A2, NR4A3, TERT, TGFB1, MMP9, CD40, CD44, HMGB1, NOS3, KDR, ITGB1, CTNNB1, CSF3, IL8, PLAUR, BCL2, BMP2, CSF1, AKT1, VEGFA, ICAM1, CXCL3, CASP8, CD34, IL1A, CD47, CCL7, HIF1A, EDN1, S1PR1, CCR1, SMAD4, FLT1, CD151, PGF, NFKB1, SMAD2, CXCR7, TGFB3, CXCL5, CCND1, HBEGF, NR3C1, TNF, ITGAL, CXCR2, STAT1, ITGA4, LIF, RASA1, CDH5, EFNB2, RGS16, CXCL2, ITGA5, CXCL12, TIMP1, FOSL2, ITGB2, and TIMP2.

In an additional embodiment, a gene expression panel is provided for identifying a population of hematopoietic cells having therapeutic potential, comprising the following genes: CREM, GEM, NR4A2, NR4A3, IL1A, COX2, HAS1, HAS1, CXCL2, CXCL3, and CXCR4.

In a further embodiment, a gene expression panel is provided for identifying a population of hematopoietic cells having therapeutic potential, comprising the following genes: CREM, GEM, NR4A2, NR4A3, IL1A, COX2, HAS1, CXCL2, CXCL3, and CXCR4.

In various embodiments, a gene expression panel is provided for identifying a population of hematopoietic cells having therapeutic potential, comprising the following genes: CREM, GEM, NR4A2, NR4A3, IL1A, COX2, HEY1, CXCL2, CXCL3, and ULBP2.

In various embodiments, a gene expression panel is provided for identifying a population of hematopoietic cells having therapeutic potential, comprising the following genes: CREM, GEM, NR4A2, NR4A3, COX2, HEY1, CXCL2, CXCL3, CXCR4, and ULBP2.

DETAILED DESCRIPTION

A. Overview

Figure 1:
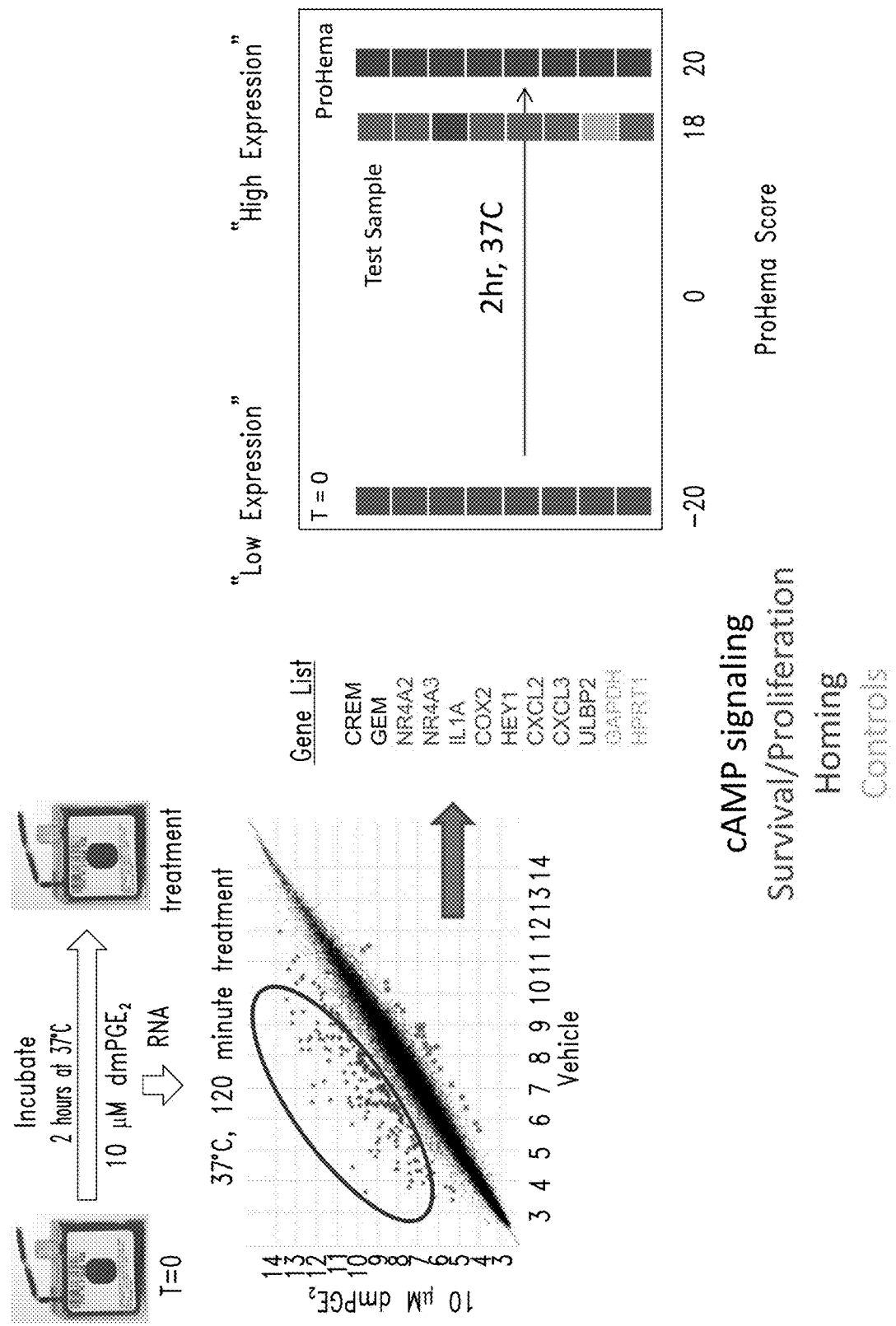
FIG. 1 shows an flow diagram of a cell potency assay.

The inventors have discovered that populations of cells having increased expression of particular groups of genes are associated with therapeutic potential in vivo, e.g., increased proliferation, increased engraftment, increased homing, and increased reconstitution. Moreover, the inventors have produced a rapid, cost-effective, reliable, and easy to use and interpret cell potency assay to measure, quantify, determine, identify, or validate the therapeutic potential in cell populations, such as, for example, whole blood samples (whole cord blood), subsets of cells isolated from the cell populations (CD34$^+$), and hematopoietic stem and progenitor cells.

In various embodiments, a cell potency assay for the therapeutic potential of a cell is contemplated. The cell potency assays are clinically important because they can be used to rapidly and reliably validate a clinical cell-based therapy product prior to administration to a subject. In effect, the framework for the cell potency assays for therapeutic potential contemplated herein are likely to become the "gold-standard" validation assay for cell therapy products that exist in the art and that are produced by the methods contemplated herein.

B. Definitions

The articles "a," "an," and "the" are used herein to refer to one or to more than one (i.e., to at least one) of the grammatical object of the article. By way of example, "an element" means one element or more than one element.

The use of the alternative (e.g., "or") should be understood to mean either one, both, or any combination thereof of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

As used herein, the term "substantially" refers to a quantity, level, value, number, frequency, percentage, dimension, size, amount, weight or length that is 90%, 92%, 93%, 94%, 95%, 96%, 97%, 98%, 99% or higher of a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

Throughout this specification, unless the context requires otherwise, the words "comprise", "comprises" and "comprising" will be understood to imply the inclusion of a stated step or element or group of steps or elements but not the exclusion of any other step or element or group of steps or elements. As used herein, the terms "include" and "comprise" are used synonymously.

By "consisting of" is meant including, and limited to, whatever follows the phrase "consisting of" Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured or modulated in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The recitations "ex vivo administration," "ex vivo treatment," or "ex vivo modulation," relate generally to medical procedures in which one or more organs, cells, or tissues are obtained from a living or recently deceased subject, optionally purified/enriched, exposed to a treatment or procedure (e.g., an ex vivo administration step that involves incubating the cells with a composition or agent of the present invention to enhance engraftment of particular cells, such as hematopoietic stem or progenitor cells). Cells treated ex vivo may be administered to the donor or to a different living subject.

Such ex vivo therapeutic applications may also include an optional in vivo treatment or procedural step, such as by administering cells with therapeutic potential one or more times to a living subject. Both local and systemic administration is contemplated for these embodiments, according to well-known techniques in the art and as described elsewhere herein. The amount of therapeutic cells administered to a subject will depend on the characteristics of that subject, such as general health, age, sex, body weight, and tolerance to drugs, as well as the degree, severity, and type of reaction to the drug and/or cell transplant.

The term "in vivo" refers generally to activities that take place inside an organism, such as cell engraftment, reconstitution, cell homing, self-renewal of cells, and expansion of cells. In one embodiment, the term "in vivo expansion" refers to the ability of a cell population to increase in number in vivo. In particular embodiments, the in vivo expansion include self-renewal and/or proliferation of stem cells.

As used herein, the term "engraftment" refers to the process of a cell integrating and becoming resident at a location, such as a tissue or site of injury. Cells may engraft in the bone marrow, for instance, or in another location such as a site of tissue injury or ischemic tissue. In particular embodiments, the term "engraftment" refers to the process of hematopoietic cells locating to the bone marrow and becoming resident cells there. In certain embodiments, engraftment is substantially independent of cell proliferation and independent of reconstitution. "Increased engraftment" occurs when more cells engraft in a onesample relative to the number of cells that engraft in a another sample, such as a control sample. In some embodiments, increased engraftment occurs when more cells in a treated sample engraft compared to the number of cells that engraft in a non-treated or control sample.

As used herein, the term "reconstitution" refers to the process of one or more engrafted hematopoietic cells repopulating or regenerating the hematopoietic system of a subject by giving rise to more progenitors and more differentiated hematopoietic cell types. In particular embodiments, reconstitution refers to the process of engrafted hematopoietic stem and/or progenitor cells repopulating the hematopoietic system. Long-term reconstitution requires engraftment. "Increased hematopoietic reconstitution" occurs when more of the hematopoietic system is reconstituted with cells in a one sample compared to cells in another sample, which may only partially or preferentially reconstitute certain hematopoietic lineages.

"Homing" refers to the ability of HSPCs to localize, i.e., travel, to a particular area or tissue. Homing may include localization of administered HSPCs to the bone marrow or to another location such as a site of injured or ischemic tissue. "Increased homing" occurs when more cells migrate to a target tissue in a one sample compared to the number of cells that migrate to the target tissue in another sample. In some embodiments, increased homing occurs when more cells in a treated sample migrate to a target tissue compared to the number of cells in a non-treated or control sample.

As used herein, the term "proliferation" refers to an increase in cell division, either symmetric or asymmetric division of cells. In particular embodiments, "proliferation" refers to the symmetric or asymmetric division of stem and/or progenitor. "Increased proliferation" occurs when there is an increase in the number of cells in a treated sample compared to cells in a non-treated sample.

As used herein, the terms "treatment," "treating," and the like, refer to obtaining a desired pharmacologic and/or physiologic effect, including without limitation achieving an improvement or elimination of symptoms of a disease. The effect may be prophylactic in terms of completely or partially preventing a disease or symptom thereof and/or may be therapeutic in terms of achieving an improvement or elimination of symptoms, or providing a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; (c) relieving the disease, e.g., causing regression of the disease, e.g., to completely or partially eliminate symptoms of the disease; and (d) restoring the individual to a pre-disease state, e.g., reconstituting the hematopoietic system.

By "enhance" or "promote," or "increase" or "activate" refers generally to the ability of an agent to produce or cause a greater physiological response (i.e., downstream effects) in a cell, as compared to the response caused by either vehicle or a control molecule/composition, e.g., increased engraftment or reconstitution of hematopoietic stem and progenitor cells and increased in vivo stem cell expansion. A measurable physiological response may include an increase in hematopoietic stem and progenitor cell engraftment, reconstitution, viability, homing, self-renewal, and/or expansion, among others apparent from the understanding in the art and the description herein. In one embodiment, the measurable physiological response includes increased expression of a plurality of genes that are markers for therapeutic potential of hematopoietic cells, compared to the expression of the genes in a reference sample (e.g., control or untreated cells). An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle (the absence of an agent) or a control composition.

By "decrease" or "lower," or "lessen," or "reduce," or "abate" refers generally to the ability of an agent to produce or cause a lesser physiological response (i.e., downstream effects) in a cell, as compared to the response caused by either vehicle or a control molecule/composition, e.g., decreased gene expression. In one embodiment, the decrease can be a decrease in gene expression or a decrease in cell signaling that normally is associated with a reduction of cell viability. An "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle (the absence of an agent) or a control composition.

By "maintain," or "preserve," or "maintenance," or "no change," or "no substantial change," "no substantial increase," or "no substantial decrease" refers generally to the ability of a agent to produce or cause a comparable physiological response (i.e., downstream effects) in a cell, as compared to the response caused by either vehicle or a control molecule/composition (reference response). A comparable response is one that is not significantly different or measurably different from the reference response.

The "therapeutic potential" of a cell refers to the therapeutic quality of the cell, the cell's ability to provide a therapeutic benefit when administered to a subject. In particular embodiments, the therapeutic potential of a cell can be measured, quantified, determined, identified, or validated by increased expression of a plurality of genes and/or by the presence of a particular gene expression signature that indicates the cell's therapeutic potential. In one embodiment, therapeutic potential refers to a cell's ability to home and engraft to a particular tissue, organ, or site of injury. In a particular embodiment, therapeutic potential refers to a cell's ability to reconstitute the hematopoietic system of a subject. In a certain embodiment, therapeutic potential refers to a cell's ability to undergo self-renewal in vivo once administered to a subject. In particular embodiments, the terms "therapeutic cell," "cell with therapeutic potential," and "cell having therapeutic potential" are used interchangeably.

In particular embodiments, cells that have increased expression of a plurality of genes and/or a particular gene expression signature have "sufficient therapeutic potential." The therapeutic potential of the cells is sufficient if they have the ability to engraft, the ability to reconstitute cell lineages, and/or the ability to proliferate when administered to a subject.

In certain embodiments, cells with therapeutic potential comprise unique or substantially unique gene and/or protein expression. The cells comprising unique or substantially unique expression are deemed to have therapeutic potential. In particular embodiments, the phrase "expression of a plurality of genes" refers to gene expression, the expression of mRNA. In other embodiments, the phrase "expression of a plurality of genes" refers to the level of protein expression.

A "plurality" of genes refers to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500 or more genes, including any intervening number of genes.

As used herein, the term "gene expression profile," "gene expression signature," "gene expression panel," "gene panel," or "gene signature" refers to the levels of expression of a plurality of genes measured for the same sample, i.e., a population of cells. A gene expression signature may be defined so as to identify a group of genes "signature genes" or a "plurality of genes" that serves to distinguish the therapeutic cells or cells having therapeutic potential from existing cells in the art and/or control, vehicle, or non-treated cells.

A "signature gene", as used herein, means any gene in a group of signature genes or plurality of genes. For clarity, signature genes do not include housekeeping genes. As used herein, the term "housekeeping gene" refers to a gene that constitutively expressed in a cell so as to maintain normal cellular functions and metabolism. Housekeeping genes are usually expressed in most, if not all tissues.

An illustrative group of genes, e.g., "signature genes" or "plurality of genes" suitable for use in particular embodiments includes, but is not limited to: hairy/enhancer-of-split related with YRPW motif 1 (HEY1), UL16 binding protein 2 (ULBP2), hyaluronan synthase 1 (HAS1), GTP-binding protein GEM (GEM), renin (REN), collagen, type I, alpha 1 (COL1A1), cyclooxygenase 2 (COX-2), angiopoietin 1 (ANGPT1), chemokine (C-X-C motif) ligand 6 (CXCL6), prominin 1 (PROM1), bone morphogenetic protein 4 (BMP4), angiopoietin 2 (ANGPT2), inhibitor of kappaB kinase beta (IKBKB), platelet/endothelial cell adhesion molecule 1 (PECAM1), tyrosine kinase with immunoglobulin-like and EGF-like domains 1 (TIE1), amphiregulin (AREG), caspase 3 (CASP3), jagged 1 (JAG1), aryl hydrocarbon receptor nuclear translocator (ARNT), cAMP-responsive element modulator (CREM), connective tissue growth factor (CTGF), CD40 ligand (CD40L), BCL2-associated X protein (BAX), hepatocyte growth factor (HGF), superoxide dismutase 2 (SOD2), platelet derived growth factor B (PDGFB), thrombospondin 1 (THBS1), dual specificity protein phosphatase 4 (DUSP4), cysteine-rich protein 61 (CYR61), chemokine (C-X-C motif) ligand 1 (CXCL1), endothelial tyrosine kinase (TEK), CASP8 and FADD-like apoptosis regulator (CFLAR), insulin growth factor 2 (IGF2), chemokine (C-X-C motif) receptor 4 (CXCR4), matrix metalloprotease 2 (MMP2), fibroblast growth factor 2 (FGF2), prostaglandin-endoperoxide synthase 2 (PTGS2), RAS-related C3 botulinum substrate 2 (RAC2), platelet derived growth factor receptor (PDGFR), nuclear receptor subfamily 4, group A, member 2 (NR4A2), nuclear receptor subfamily 4, group A, member 3 (NR4A3), telomerase reverse transcriptase (TERT), transforming growth factor beta 1 (TGFB1), matrix metalloprotease 9 (MMP9), CD40 antigen (CD40), CD44 antigen (CD44), high mobility group box 1 (HMGB1), nitrogen oxide synthase 3 (N053), kinase insert domain receptor (KDR), integrin beta 1 (ITGB1), catenin (cadherin-associated protein), beta 1 (CTNNB1), colony stimulating factor 3 (CSF3), interleukin 8 (IL8), plasminogen activator, urokinase receptor (PLAUR), B-cell CLL/lymphoma 2 (BCL2), bone morphogenetic protein 2 (BMP2), colony stimulating factor 1 (CSF1), v-akt murine thymoma viral oncogene homolog 1 (AKT1), vascular endothelial growth factor A (VEGFA), intercellular adhesion molecule 1 (ICAM1), chemokine (C-X-C motif) ligand 3 (CXCL3), caspase 8 (CASP8), CD34 antigen (CD34), interleukin 1A (IL1A), CD47 antigen (CD47), chemokine (C-C motif) ligand 7 (CCL7), hypoxia inducible factor 1A (HIF1A), EDN1 (endothelin 1), sphingosine-1-phosphate receptor 1 (S1PR1), chemokine (C-C motif) receptor 1 (CCR1), SMAD family member 4 (SMAD4), fms-related tyrosine kinase 1 (FLT1), CD151 antigen (CD151), placental growth factor (PGF), nuclear factor of kappa light polypeptide gene enhancer in B-cells 1 (NFKB1), SMAD family member 2 (SMAD2), CXC chemokine receptor 7 (CXCR7), transforming growth factor beta 3 (TGFB3), chemokine (C-X-C motif) ligand 5 (CXCL5), cyclin D1 (CCND1), heparin-binding EGF-like growth factor (HBEGF), nuclear receptor subfamily 3, group C, member 1 (NR3C1), tumor necrosis factor (TNF), integrin alpha L (ITGAL), CXC chemokine receptor 2 (CXCR2), signal transducer and activator of transcription 1 (STAT1), integrin alpha 4 (ITGA4), leukemia inhibitory factor (LIF), RAS p21 protein activator 1 (RASA1), cadherin 5 (CDH5), ephrin B2 (EFNB2), regulator of G-protein signaling 16 (RGS16), chemokine (C-X-C motif) ligand 2 (CXCL2), integrin alpha 5 (ITGA5), chemokine (C-X-C motif) ligand 12 (CXCL12), tissue inhibitor of metalloprotease 1 (TIMP1), Fos-related antigen 2 (FOSL2), integrin beta 2 (ITGB2), and tissue inhibitor of metalloprotease 2 (TIMP2).

Another illustrative group of genes, e.g., "signature genes" or "plurality of genes" suitable for use in particular embodiments includes, but is not limited to: hairy/enhancer-of-split related with YRPW motif 1 (HEY1), UL16 binding protein 2 (ULBP2), cyclooxygenase 2 (COX-2), hyaluronan synthase 1 (HAS1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), Fos-related antigen 2 (FOSL2), and CXC chemokine receptor 4 (CXCR4).

A further illustrative group of genes, e.g., "signature genes" or "plurality of genes" suitable for use in particular embodiments includes, but is not limited to: HEY1, ULBP2, CREM, GEM, NR4A2, NR4A3, IL1A, COX2, HAS1, CXCL2, CXCL3, and CXCR4.

A further illustrative group of genes, e.g., "signature genes" or "plurality of genes" suitable for use in particular embodiments includes, but is not limited to: CREM, GEM, NR4A2, NR4A3, IL1A, CXCL2, CXCL3, HEY1, COX2, and ULBP2.

"Gene expression" as used herein refers to the relative levels of expression and/or pattern of expression of a gene in a biological sample, such as the stem and progenitor cells, or population of cells comprising stem or progenitor cells. In particular embodiments, the stem or progenitor cells are hematopoietic stem and progenitor cells.

"Genetic modification" refers to a temporary or permanent modification of a cell's genome, for example by insertion of a polynucleotide sequence in a viral or plasmid vector, or by homologous recombination or non-homologous end joining.

As used herein, the term "gene therapy" refers to the introduction of a polynucleotide into a cell that restores, corrects, or modifies the gene and/or expression of the gene. In particular embodiments, the polynucleotide is incorporated into the cell's genome and in other embodiments, the polynucleotide is episomal.

As used herein, the phrases "detecting expression," "determining expression," and "measuring expression" refer to determining the quantity or presence of an RNA transcript or its expression product of a gene. Methods for detecting expression of genes, that is, gene expression profiling, include methods based on hybridization analysis of polynucleotides, methods based on sequencing of polynucleotides, immunohistochemistry methods, and proteomics-based methods. The methods generally detect expression products (e.g., mRNA) of the genes of interest. In some embodiments, PCR-based methods, such as reverse transcription PCR (RT-PCR) (Weis et al., TIG 8:263-64, 1992), and array-based methods such as microarray (Schena et al., Science 270:467-70, 1995) are used.

General methods for RNA extraction are well known in the art and are disclosed in standard textbooks of molecular biology, including Ausubel et al., ed., Current Protocols in Molecular Biology, John Wiley & Sons, New York 1987-1999. In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns. Isolated RNA can be used in hybridization or amplification assays that include, but are not limited to, PCR analyses and probe arrays. One method for the detection of RNA levels involves contacting the isolated RNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 60, 100, 250, or 500 nucleotides in length and sufficient to specifically hybridize under stringent conditions to an intrinsic gene of the present invention, or any derivative DNA or RNA. Hybridization of an mRNA with the probe indicates that the intrinsic gene in question is being expressed.

An alternative method for determining the level of gene expression in a sample involves the process of nucleic acid amplification, for example, by RT-PCR (U.S. Pat. No. 4,683, 202), ligase chain reaction (Barany, Proc. Natl. Acad. Sci. USA 88:189-93, 1991), self sustained sequence replication (Guatelli et al., Proc. Natl. Acad. Sci. USA 87:1874-78, 1990), transcriptional amplification system (Kwoh et al., Proc. Natl. Acad. Sci. USA 86:1173-77, 1989), Q-Beta Replicase (Lizardi et al., Bio/Technology 6:1197, 1988), rolling circle replication (U.S. Pat. No. 5,854,033), or any other nucleic acid amplification method, followed by the detection of the amplified molecules using techniques well known to those of skill in the art.

Numerous different PCR or qPCR protocols are known in the art and exemplified herein below and can be directly applied or adapted for use using the cell potency assays contemplated herein to determine therapeutic potential. Quantitative PCR (qPCR) (also referred as real-time PCR) is preferred under some circumstances because it provides not only a quantitative measurement, but also reduced time and contamination. In some instances, the availability of full gene expression profiling techniques is limited due to requirements for fresh frozen tissue and specialized laboratory equipment, making the routine use of such technologies difficult in a clinical setting. As used herein, "quantitative PCR (or "real time qPCR") refers to the direct monitoring of the progress of PCR amplification as it is occurring without the need for repeated sampling of the reaction products. In quantitative PCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence varies directly with the concentration of amplifiable targets at the beginning of the PCR process, enabling a measure of signal intensity to provide a measure of the amount of target nucleic acid in a sample in real time.

C. Cell Potency Assays

Cell potency assays contemplated herein measure, determine, identify, confirm, and/or validate the therapeutic potential of cell-based products. Populations of cells with therapeutic potential have therapeutic properties, e.g., engraftment, reconstitution, and/or proliferation. Populations of enhanced cells with increased therapeutic potential have increased therapeutic properties, e.g., engraftment, reconstitution, and/or proliferation. The invention provides cell potency assays that can rapidly and reliably determine, confirm, or validate cell-based products having a desired therapeutic potential.

Cell potency assays contemplated herein comprise measuring or determining the expression of a plurality of genes in a population of cells and identifying increased expression of the plurality of genes, wherein increased expression of two or more of the plurality of genes indicates that the cell population has sufficient therapeutic potential. The inventors have discovered a panel of about 100 genes whose expression indicates therapeutic potential of hematopoietic cell populations. In addition, the inventors have identified subsets of the gene panel that also indicate the therapeutic potential of the hematopoietic cell populations. The subsets comprise from 2 genes to about 50 genes, from 2 genes to about 25 genes, from 2 genes to about 20 genes, from 2 genes to about 15 genes, from 2 genes to about 12 genes, from 2 genes to about 10 genes, from 2 genes to about 5 genes, or any intervening range of genes therebetween.

In one embodiment, the cell potency assay or method comprises determining the therapeutic potential of a population of cells by determining a gene expression profile. The method can be practiced in vitro or in vivo and on cell populations that have or have not been treated with one or more agents that increase the therapeutic potential of a cell population.

In particular embodiments, the therapeutic potential of cell populations correlates with increased expression of a plurality of genes or with a particular gene expression signature. In certain embodiments, treatment of a cell population with one or more agents increases the therapeutic potential of the treated cells and the associated gene expression compared to non-treated, untreated, or control cells. Treated cells may further have an increased ability to engraft, reconstitute, and proliferate in vivo compared to non-treated, untreated, or control cells.

In particular embodiments, cell potency assays that determine therapeutic potential comprise measuring the gene expression profile or the expression of a plurality of genes in a population of cells and identifying increased expression in at least one or at least two genes in the gene expression profile or in the plurality of genes.

In one preferred embodiment, the cell potency assay comprises determining the therapeutic potential of a population of cells by identifying increased expression of all genes in a gene expression profile or in a plurality of genes. In particular embodiments, a cell potency assay identifies the therapeutic potential of a population of cells if the expression of two or more genes in the gene expression signature or in the plurality of genes is increased at least two-fold compared to the expression of the same genes in control cells.

Cell potency assays contemplated herein determine or identify therapeutic potential of cell populations that have increased expression of a plurality of genes in a gene expression signature or panel. One illustrative example of a suitable gene expression panel for use in the cell potency assays disclosed herein includes HEY1, COX2, ULBP2, HAS1, GEM1, REN, COL1A1, ANGPT1, CXCL6, PROM1, BMP4, ANGPT2, IKBKB, PECAM1, TIE1, AREG, CASP3, JAG1, ARNT, CREM, CTGF, CD40L, BAX, HGF, SOD2, PDGFB, THBS1, DUSP4, CYR61, CXCL1, TEK, CFLAR, IGF2, CXCR4, MMP2, FGF2, PTGS2, RAC2, PDGFR, NR4A2, NR4A3, TERT, TGFB1, MMP9, CD40, CD44, HMGB1, NOS3, KDR, ITGB1, CTNNB1, CSF3, IL8, PLAUR, BCL2, BMP2, CSF1, AKT1, VEGFA, ICAM1, CXCL3, CASP8, CD34, IL1A, CD47, CCL7, HIF1A, EDN1, S1PR1, CCR1, SMAD4, FLT1, CD151, PGF, NFKB1, SMAD2, CXCR7, TGFB3, CXCL5, CCND1, HBEGF, NR3C1, TNF, ITGAL, CXCR2, STAT1, ITGA4, LIF, RASA1, CDH5, EFNB2, RGS16, CXCL2, ITGA5, CXCL12, TIMP1, FOSL2, ITGB2, and TIMP2.

In one non-limiting example, cell potency assays measure or determine the expression of a plurality of the signature genes selected from the group consisting of: CREM, GEM, NR4A2, NR4A3, IL1A, COX2, HAS1, CXCL2, CXCL3, HEY1, ULBP2, and CXCR4 to identify a cell population with therapeutic potential.

In a particular embodiment, cell potency assays measure or determine the expression in whole cord blood cells of a plurality of the signature genes selected from the group consisting of: CREM, GEM, NR4A2, NR4A3, IL1A, CXCL2, CXCL3, HEY1, COX2, and ULBP2. In a particular embodiment, cell potency assays measure or determine the expression in whole cord blood cells of a plurality of the signature genes comprising: CREM, GEM, NR4A2, NR4A3, IL1A, CXCL2, CXCL3, HEY1, COX2, and ULBP2.

In a particular embodiment, cell potency assays measure or determine the expression in isolated CD34+ cells of a plurality of the signature genes selected from the group consisting of: CREM, GEM, NR4A2, NR4A3, CXCL2, CXCL3, HEY1, CXCR4, COX2, and ULBP2. In a particular embodiment, cell potency assays measure or determine the expression in isolated CD34+ cells of a plurality of the signature genes comprising: CREM, GEM, NR4A2, NR4A3, CXCL2, CXCL3, HEY1, CXCR4, COX2, and ULBP2.

Therapeutic potential may be indicated by increased expression of 2, 3, 4, 5, 6, 7, 8, 9, or 10 signature genes compared to expression levels in control or untreated cells.

In particular embodiments, cell potency assays can identify cells with therapeutic potential by measuring increased expression of at least two genes, at least five genes, at least 10 genes, at least 25 genes, at least 50 genes, or at least 100 or more genes, or any intervening number of signature genes. In preferred embodiments, cell potency assays can identify cells with therapeutic potential by measuring increased expression of about 2 to about 25 genes, about 2 to about 10 genes, or about 5 to about 10 genes, or any intervening range of genes thereof.

In certain embodiments, cell potency assays determine that a cell population has therapeutic potential if two or more genes of a gene expression panel or plurality of genes has increased expression compared to expression of the genes in a control population of cells. In particular embodiments, the cell potency assays contemplated herein identify the therapeutic potential of a cell population when the expression of at least 2, 3, 4, or 5 genes is increased about 80-fold, about 70-fold, about 60-fold, about 50-fold, about 40-fold, about 30-fold, about 20-fold, about 10-fold, about 5-fold, about 3-fold, or about 2-fold compared to expression of the genes in a control population cells. In additional embodiments, the cell potency assays contemplated herein identify the therapeutic potential of a cell population when the expression of at least 10, 20, 30, 40, 50, 60, 70, 80, or 90 genes, or any intervening number of genes thereof, is increased about 80-fold, about 70-fold, about 60-fold, about 50-fold, about 40-fold, about 30-fold, about 20-fold, about 10-fold, about 5-fold, about 3-fold, or about 2-fold compared to expression of the genes in a control population cells.

In one embodiment, the assay or method comprises measuring expression of two or more genes of a gene expression signature, gene panel, or plurality of genes in a population of cells; calculating a score for the expression measured for the genes, wherein the score indicates the therapeutic potential of the population of cells; and comparing the score to a predetermined cut-off. If the score is greater than or equal to the cut-off score, the cell population is identified as having sufficient therapeutic potential; whereas, if the score is lower than the cut-off score, the cell population is identified as having insufficient therapeutic potential. In particular embodiments, the cut-off is a pre-determined cut-off.

Without wishing to be bound to any particular theory, the cut-off score for therapeutic potential (e.g., sufficient therapeutic potential) may be determined by calculating gene expression scores for a plurality of genes for both cells that lack therapeutic potential and those with optimal therapeutic potential. The cut-off score can then be assigned according to the therapeutic properties exhibited by the cells having therapeutic potential, e.g., increased engraftment, increased reconstitution, and increased proliferation. Accordingly, the score calculated using the cell potency assay to measure the therapeutic potential of a cell population can then be compared to the cut-off score and it can be determined whether the cell population has therapeutic potential.

In one illustrative embodiment, a cell potency assay to identify a cell population with increased therapeutic potential comprises the use of polymerase chain reaction (PCR), such as, for example, real-time quantitative PCR (RT-qPCR) or quantitative PCR (qPCR), to determine or measure the gene expression of one or more genes in a gene signature, gene panel, or plurality of genes. Mean Ct (cycle threshold) values of replicate qPCR reactions for one or more signature genes and one or more housekeeping genes are determined Mean Ct values for each signature gene is then normalized to the Ct values of the housekeeping genes using the following illustrative formula: signature gene$_X$ΔCt=(mean Ct of signature gene$_X$−((mean Ct of housekeeping gene$_A$+ mean Ct of housekeeping gene$_B$)/2); wherein X is each signature gene. Distribution models of signature gene specific ΔCt values can then be calculated based on gene expression data obtained from control cells and cells with increased therapeutic potential.

ΔCt values can then be calculated for signature genes in a cell population being assayed using the cell potency assays contemplated herein. The ΔCt values for the signature genes are then standardized against the signature gene specific ΔCt distribution model for both the control cells and the cells with increased therapeutic potential. Standardized Euclidean distance calculations can then be performed with the standardized ΔCt values for the signature genes against the distribution models for both the control cells and the cells with optimal therapeutic potential using the following illustrative formula:

$$d_{x,\mu} = \sqrt{\sum_{j=1}^{n}(x_j-\mu_j)^2}$$

to determine expression similarities.

The two Standardized Euclidean distance calculations (genes relative to control condition and genes relative to optimal condition) are then median centered and converted into a single score using the following illustrative formula: score=Euclidean distance$_{control}$−Euclidean distance$_{optimal}$. A large score indicates that the test cells cluster close to the control optimal increased therapeutic cells; whereas a small score indicates that the test cells cluster closer to the control cells. Accordingly, if a cell population score is large enough, such that it is greater than the cut-off score for cells having increased therapeutic potential, the cell potency assays contemplated herein would identify the cell population as having increased therapeutic potential.

D. Cells

Cell potency assays contemplated herein are useful for determining the therapeutic potential of any therapeutic cell population including, but not limited to stem cells, progenitor cells, and differentiated cells. The assayed cells may comprise embryonic stem cells, bone marrow stem cells, umbilical cord stem cells, placental stem cells, mesenchymal stem cells, neural stem cells, liver stem cells, pancreatic stem cells, cardiac stem cells, T cells, kidney stem cells, hematopoietic stem cells and muscle stem cells.

In various embodiments, the use of stem cells is preferred because they have the ability to differentiate into the appropriate cell types when administered to a particular biological niche, in vivo. The term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. "Self-renewal" refers a cell with a unique capacity to produce unaltered daughter cells and to generate specialized cell types (potency). Self-renewal can be achieved in two ways. Asymmetric cell division produces one daughter cell that is identical to the parental cell and one daughter cell that is different from the parental cell and is a progenitor or differentiated cell. Asymmetric cell division does not increase the number of cells. Symmetric cell division produces two identical daughter cells. "Proliferation" or "expansion" of cells refers to symmetrically dividing cells.

As used herein, the term "progenitor" or "progenitor cells" refers to cells that have the capacity to self-renew and to differentiate into more mature cells. Progenitor cells have a reduced potency compared to pluripotent and multipotent stem cells. Many progenitor cells differentiate along a single lineage, but may also have quite extensive proliferative capacity.

Cells being assayed for therapeutic potential include autologous/autogeneic ("self") or non-autologous ("non-self," e.g., allogeneic, syngeneic or xenogeneic) cells. "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells of the invention are allogeneic.

Cells can undergo a number of manipulations prior to being assayed. For example, cells can be modulated in vitro or ex vivo with one or more agents to increase the therapeutic potential of the cells; cells can be expanded in vitro or ex vivo with one or more agents before or after cells are treated with one or more agents to increase therapeutic potential. In some embodiments, expansion of the cells increases the therapeutic potential. Cells can also be cryopreserved prior to or after modulation with one or more agents to increase therapeutic potential and/or expand the cell population.

In various embodiments, the cells are not genetically modified cells. In other embodiments, the cells are genetically modified with a polynucleotide, such as, for example a retroviral or lentiviral vector comprising a protein coding gene sequence. In some embodiments, the cell is genetically modified to correct a genetic defect and in other embodiments, the cell is genetically modified to increase or decrease production of a wild-type or mutant protein. Polynucleotides used to increase expression of a protein in a cell may comprise polynucleotide sequences to direct appropriate expression in the cell and a polynucleotide encoding the polypeptide sequence. Polynucleotides used to decrease expression of a protein in a cell may comprise polynucleotide sequences that target polynucleotides encoding the wild type polypeptide sequence for degradation.

The therapeutic potential of hematopoietic cells is important in various cell-based therapies. Populations of cells comprising hematopoietic cells having sufficient therapeutic potential are suitable for administration to a subject and demonstrate increased engraftment, reconstitution, and cell proliferation, in vivo. Cell populations include whole blood samples, e.g., whole cord blood, whole mobilized peripheral blood, whole bone marrow samples; isolated cells expressing particular markers, e.g., CD34$^+$; and hematopoietic stem and progenitor cells. Populations of cells comprising hematopoietic cells include bone marrow cells, umbilical cord blood cells, placental blood cells, mobilized peripheral blood cells, hematopoietic stem cells, or hematopoietic progenitor cells. In particular embodiments, the therapeutic potential of a population of cells comprising hematopoietic stem and/or progenitor cells (HPSCs) is measured, quantified, determined, identified, or validated using the inventive methods disclosed herein.

In one embodiment, the amount of cells assay is at least $1\times10^3$ cells, at least $1\times10^4$ cells, at least $1\times10^5$ cells, at least $1\times10^6$ cells, at least $1\times10^7$ cells or any intervening number of cells.

In particular embodiments, a cell potency assay may determine the therapeutic potential of a population of cells that is about 95% to about 100% HSPCs. In some embodiments, the population of cells comprises less than about 0.1%, 0.5%, 1%, 2%, 5%, 10%, 15%, 20%, 25%, or 30% HSPCs. The population of cells in some embodiments comprises less than about 0.1%, 0.5%, 1%, 2%, 5%, 10%, 15%, 20%, 25%, or 30% HSPCs. In other embodiments, the population of cells is about 0.1% to about 1%, about 1% to about 3%, about 3% to about 5%, about 10%-about 15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% HSPCs.

In particular embodiments, the population of cells is about 0.1% to about 1%, about 1% to about 3%, about 3% to about 5%, about 10%-about 15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% HSPCs.

Hematopoietic stem cells are multipotent stem cells that give rise to all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827). Hematopoietic progenitor cells (HSCs) give rise to committed hematopoietic progenitor cells (HPCs) that are capable of generating the entire repertoire of mature blood cells over the lifetime of an organism.

As used herein, the term "hematopoietic stem and progenitor cell" or "HSPC" refers to a cell identified by the presence of the antigenic marker CD34 (CD34$^+$) and are therefore characterized as CD34$^+$ cells, and populations of such cells. In particular embodiments, the term "HSPC" refers to a cell identified by the presence of the antigenic marker CD34 (CD34$^+$) and the absence of lineage (Lin) markers and are therefore characterized as CD34$^+$/Lin(−) cells, and populations of such cells. It is recognized that the population of cells comprising CD34$^+$ and/or Lin(−) cells also includes hematopoietic progenitor cells.

The therapeutic potential of HPSCs isolated from any suitable source can be measured or determined by the inventive methods disclosed herein. In addition, the therapeutic potential of both treated and non-treated hematopoietic cell populations can be determined. In particular embodiments, HPSCs can be provided as a highly purified HSPC population (a homogenous population), or as a composition that comprises from 0.01% to about 100% of HSPCs (a heterogeneous population). Suitable HPSC sources include, but are not limited to bone marrow, umbilical cord blood, placental blood, placenta, fetal blood, fetal liver, fetal spleen, Wharton's jelly, or mobilized peripheral blood. In particular embodiments, harvesting a sufficient quantity of HSPCs for use in therapeutic applications may require mobilizing the stem and progenitor cells in the donor.

As used herein, the term "isolated" refers to material that is removed from its original environment. For example, an "isolated population of cells," an "isolated source of cells," or "isolated HSPCs" and the like, as used herein, refer to in vitro or ex vivo separation of one or more cells from their natural cellular environment, and from association with other components of the tissue or organ, i.e., it is not significantly associated with in vivo substances.

"Hematopoietic stem cell mobilization" refers to the release of stem cells from the bone marrow into the peripheral blood circulation for the purpose of leukapheresis, prior to transplantation. Hematopoietic growth factors, e.g., granulocyte colony stimulating factor (G-CSF) or chemotherapeutic agents often are used to stimulate the mobilization. Commercial stem cell mobilization drugs, e.g., Mozobil™, can be used in combination with G-CSF to mobilize sufficient quantities of HPSCs for transplantation into a subject.

In particular embodiments, HSPCs are obtained from umbilical cord blood. Cord blood can be harvested according to techniques known in the art (see, e.g., U.S. Pat. Nos. 7,147,626 and 7,131,958, herein incorporated by reference for such methodologies).

In particular embodiment, compositions comprise populations of cells that are HLA typed and may be matched or partially matched to a specific patient for transplantation. HLA-type refers to the unique set of proteins called human leukocyte antigens. These proteins are present on each individual's cells and allow the immune system to recognize 'self' from 'foreign'. Administration of cells or tissues that are recognized as foreign can lead to compatibility problems such as immuno-rejection or graft versus host disease (GVHD). Accordingly, HLA type and matching is particularly important in organ and tissue transplantation.

There are six major HLAs (HLA-A, HLA-B, HLA-C, HLA-DR, HLA-DP, and HLA-DQ). Each HLA antigen has multiple isoforms in the human population, and each individual can have two different isoforms for each HLA due to the diploid nature of our genome. Therefore, a complete match would match twelve out of twelve isoforms. A cell or tissue donated from the same individual as, or an identical twin of, the intended recipient would have a perfect HLA-type and is referred to as syngeneic or autologous. It is also understood that certain factors including but not limited to ethnic background and race correlate with certain HLA-types.

HLA-type can be determined using so-called low resolution methods, for example by sero-typing, or using antibody based methods. Sero-typing is based on antibody recognition of HLA-types. Sero-typing can distinguish between 28 different HLA-A genes, 59 HLA-B genes and 21 HLA-C genes. A perfect match by sero-typing methods would be a so-called six out of six match referring to the two alleles for each HLA (A, B, and C) present in each individual. In certain cases, a five out of six match or less may be considered a good match as determined by one skilled in the art.

At a minimum, HLA typing of the cell population is performed for six HLA loci, HLA-A, -B, and -DR, for example, at low resolution/split antigen level.

In various embodiments, the population of cells comprises haplotyped hematopoietic stem or progenitor cells. In some embodiments, the population of cells is HLA typed based on HLA-A, HLA-B, HLA-C, and HLA-DRB1. In particular embodiments, the population of cells is HLA typed based on the group consisting of HLA-DRB3/4/5, HLA-DQB1, and DPB1. In some embodiments, the population of cells is matched with a specific human patient. In some embodiments, the population of HLA haplotyped cells has 4 out of 6 HLA matches with a specific human subject. HLA matching may be based on alleles or antigens, and combinations thereof. In some embodiments, the population of HLA haplotyped cells is a partial mismatch with a specific human subject, such as the subject to which the therapeutic composition is administered.

E. Methods of Preparing Cells

In various embodiments, cell potency assays contemplated herein comprise determining or measuring the expression of two or more genes of a gene expression signature or plurality of genes in a population of treated cells to determine, confirm, or validate the therapeutic potential of the cells. In certain embodiments, the gene expression of the treated cells is compared to the gene expression of the cells before treatment or to the gene expression in untreated or control cells. As used herein, a "non-contacted," "non-treated," or an "untreated" cell is a cell that has not been treated, e.g., cultured, contacted, or incubated with an agent other than a control agent. Cells contacted with DMSO (a control agent), or contacted with another vehicle are non-contacted cells.

Expression may be determined after cells are treated with an agent, or cells may be incubated for some period of time after treatment before determining the gene expression signature of the cells. For example, cells may be treated in vitro or ex vivo with one or more agents, washed to remove the agents, and the gene expression analyzed without further incubation of the cells. Alternatively, in some embodiments, cells are treated with one or more agents, washed to remove the agents from the cell population, and then the cells are incubated in vitro or ex vivo for some period of time prior to analyzing the gene expression signature of the cells.

As used herein, the terms "conditions sufficient," or "under conditions sufficient," refer to the conditions for treating cells with one or more agents to increase gene expression in the cells to surprising and unexpected levels compared to control, vehicle, or non-treated cells, such that the treated cells acquire therapeutic potential. Conditions include, but are not limited to the agents used to treat the cells and concentrations of agent(s), the time the cells are exposed to the agent(s), and the temperature of treatment.

As used herein, "agent" refers to a compound or molecule capable of increasing expression of two or more genes in a particular gene expression signature or plurality of genes. In particular embodiments, the agent increases gene expression in cells, e.g., hematopoietic cells, and increases the therapeutic potential of the cells. In particular embodiments, a combination of two or more agents acts synergistically to increase gene expression in cells and increases the therapeutic potential of the cells.

Particular agents for modulating hematopoietic cells, e.g., HSPCs, include, for example, prostaglandin pathway agonists selected from the group consisting of a cAMP analogue or enhancer, a Ga-s activator, and a compound that selectively binds the $PGE_2$ $EP_2$ or the $PGE_2$ $EP_4$ receptor; and glucocorticoids.

As used herein, the term "prostaglandin pathway agonist" refers to an agent that stimulates prostaglandin cell signaling pathways, including an agent that stimulates the $PGE_2R_2$ and/or $PGE_2R_4$ cell signaling pathways. Illustrative examples of prostaglandin pathway agonists that are suitable for use in preparing cells of the invention, include, but are not limited to, $PGE_2$, $dmPGE_2$, 15(S)-15-methyl $PGE_2$, 20-ethyl $PGE_2$, 8-iso-16-cyclohexyl-tetranor $PGE_2$, and $PGE_2$ analogues. In certain embodiments, $PGE_2R_2$ and $PGE_2R_4$ agonists and analogues thereof are of particular interest, and in some embodiments, the agent preferentially binds and activates a $PGE_2$ $EP_2$ or $PGE_2$ $EP_4$ receptor.

As used herein, the terms "prostaglandin $E_2$" or "$PGE_2$" include, without limitation, any naturally-occurring or chemically synthesized $PGE_2$ molecule, as well as "analogues" thereof. As used herein, the term "analogue" or relates to a chemical molecule that is similar to another chemical substance, e.g., $PGE_2$, in structure and function, often differing structurally by a single element or group, but may differ by modification of more than one group (e.g., 2, 3, or 4 groups) if it retains the same function as the parental chemical.

Illustrative examples of $PGE_2$ "analogues" include, without limitation, 16,16-dimethyl $PGE_2$ ("$dmPGE_2$"), 16,16-dimethyl $PGE_2$ p-(p-acetamidobenzamido) phenyl ester, 11-deoxy-16,16-dimethyl $PGE_2$, 9-deoxy-9-methylene-16,16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15(R)-15-methyl $PGE_2$, 8-iso-15-keto $PGE_2$, 8-iso $PGE_2$ isopropyl ester, 8-iso-16-cyclohexyl-tetranor $PGE_2$, 20-hydroxy $PGE_2$, 20-ethyl $PGE_2$, 11-deoxy $PGE_1$, nocloprost, sulprostone, butaprost, 15-keto $PGE_2$, and 19 (R) hydroxy $PGE_2$. Also included are prostaglandin analogues having a similar structure to $PGE_2$ that are substituted with halogen at the 9-position (see, e.g., WO 2001/12596, herein incorporated by reference in its entirety), as well as 2-decarboxy-2-phosphinico prostaglandin derivatives, such as those described in U.S. Publication No. 2006/0247214, herein incorporated by reference in its entirety).

$PGE_1$ analogues, including without limitation alprostadil, can also be used to activate the $PGE_2R_2$ ($EP_2$) and $PGE_2R_4$ ($EP_4$) cell signaling pathways, and are contemplated as agents useful in the methods of the invention.

Stimulation/activation of the $PGE_2R_2$ ($EP_2$) and $PGE_2R_4$ ($EP_4$) cell signaling pathways are contemplated to underlie the physiological responses in HSPCs that increase engraftment, reconstitution, and proliferation of the cells. Accordingly, in one embodiment, a "non-$PGE_2$-based ligand" that binds to and stimulates PGE$_2$R$_2$ and PGE$_2$R$_4$ receptors (i.e., a PGE$_2$R$_2$/PGE$_2$R$_4$ agonist) is contemplated for use in the methods of the invention.

Illustrative examples of non-PGE$_2$-based EP$_2$ receptor agonists include CAY10399, ONO_8815Ly, ONO-AE1-259, CP-533,536 and carbazoles and fluorenes disclosed in WO 2007/071456.

Illustrative examples of non-PGE$_2$-based EP$_4$ agonists include ONO-4819, APS-999 Na, AH23848, ONO-AE1-329, and other non-PGE$_2$-based EP$_4$ agonists disclosed in WO/2000/038663; U.S. Pat. Nos. 6,747,037; and 6,610,719).

Agents selective for the PGE$_2$ EP$_4$ receptor preferentially bind to and activate PGE$_2$ EP$_4$ receptors. Such agents have a higher affinity for the EP$_4$ receptor than for any of the other three EP receptors namely EP$_1$, EP$_2$ and EP$_3$. Agents that selectively bind the PGE EP$_4$ receptor include, but are not limited to, agents selected from the group consisting of: 5-[(1E,3R)-4,4-difluoro-3-hydroxy-4-phenyl-1-buten-1-yl]-1-[6-(2H-tetrazol-5R-yl)hexyl]-2-pyrrolidinone; 2-[3-[(1R,2S,3R)-3-hydroxy-2-[(E,3S)-3-hydroxy-5-[2-(methoxymethyl)phenyl]pent-1-enyl]-5-oxocyclopentyl]sulfanylpropylsulfanyl]acetic acid; methyl 4-[2-[(1R,2R,3R)-3-hydroxy-2-[(E,3S)-3-hydroxy-4-[3-(methoxymethyl)phenyl]but-1-enyl]-5-oxocyclopentyl]ethylsulfanyl]butanoate; 16-(3-Methoxymethyl)phenyl-ro-tetranor-5-thiaPGE; 5-{3-[(2S)-2-{(3R)-3-hydroxy-4-[3-(trifluoromethyl)phenyl]butyl}-5-oxopyrrolidin-1-yl]propyl]thiophene-2-carboxylate; [4'-[3-butyl-5-oxo-1-(2-trifluoromethyl-phenyl)-1,5-dihydro-[1,2,4]triazol-4-ylmethyl]-biphenyl-2-sulfonic acid (3-methyl-thiophene-2-carbonyl)-amide]; and ((Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid), and pharmaceutically acceptable salts of any of these agents.

In particular embodiments, the prostaglandin pathway agonist is PGE$_2$, 16,16-dmPGE$_2$, 15(S)-15-methyl PGE$_2$, 20-ethyl PGE$_2$, or 8-iso-16-cyclohexyl-tetranor PGE$_2$.

Cell potency assays contemplated herein can also be used to determine the therapeutic potential of hematopoietic cells treated with a prostaglandin pathway agonist and a glucocorticoid.

Illustrative examples of glucocorticoids and glucocorticoid receptor agonists suitable for use in the methods of the invention include, but are not limited to, medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methyl-prednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol, as well as combinations thereof.

In particular embodiments, the glucocorticoid comprises medrysone, hydrocortisone, triamcinolone, alclometasone, or dexamethasone. In more particular embodiments, the glucocorticoid is medrysone.

In particular embodiments, cell potency assays contemplated herein comprise determining, measuring, confirming, or validating the therapeutic potential of treated cells. In one embodiment, cells are treated with one or more agents, in an amount effective and for a time sufficient (i.e., under conditions sufficient) to increase therapeutic potential of the cells. The therapeutic potential of the treated cells can then be determined, measured, confirmed, or validated using the methods contemplated herein.

In various embodiments, sufficient temperature conditions to increase therapeutic potential include incubation of the cells with the one or more agents at a physiologically relevant temperature, such as a temperature range of about 22° C. to about 39° C. (about room temperature to about body temperature), including but not limited to temperatures of about 22° C., 23° C., 24° C., 25° C., 26° C., 27° C., 28° C., 29° C., 30° C., 31° C., 32° C., 33° C., 34° C., 35° C., 36° C., 37° C., 38° C., and 39° C. In a particular embodiment, the sufficient temperature condition is between about 35° C. and 39° C. In one embodiment, the sufficient temperature condition is about 37° C.

In particular embodiments, a sufficient concentration of an agent to increase therapeutic potential is a final concentration of about 10 nM to about 100 μM, about 100 nM, about 500 nM, about 1 μM, about 10 μM, about 20 μM, about 30 μM, about 40 μM, about 50 μM, about 60 μM, about 70 μM, about 80 μM, about 90 μM, about 100 μM, about 110 μM, or about 120 μM, or any other intervening concentration of the agent (e.g., 0.1 μM, 1 μM, 5 μM, 10 μM, 20 μM, 50 μM, 100 μM). In a particular embodiment, the sufficient concentration of each agent is a final concentration of about 10 μM to about 25 μM. In one embodiment, the sufficient concentration of an agent is a final concentration of about 10 μM.

In certain embodiments, the sufficient time period for treating cells with one or more agents to increase therapeutic potential is an incubation period of about 60 minutes to about 24 hours, about 60 minutes to about twelve hours, about 60 minutes to about 6 hours, about 2 hours to about 6 hours, about 2 hours to about 4 hours, and including, but not limited to, treatment for a duration of about 60 minutes, about 70 minutes, about 80 minutes, about 90 minutes, about 100 minutes, about 110 minutes, about 2 hours, about 2.5 hours, about 3 hours, about 3.5 hours or about 4 hours or any other intervening duration. In a particular embodiment, the sufficient incubation period is about 2 hours to about 4 hours. In one embodiment, the sufficient incubation period for treating the cells is about four hours.

In particular embodiments, hematopoietic cells having therapeutic potential have been modulated under conditions sufficient to increase gene expression of about 2, 5, 10, 25, 50, 75, or 100 signature genes at least 2, 3, 5, 10, 20, 30, 40, 50, 60, 70, or 80 fold in the modulated cells compared to control cells, the conditions comprising treating HSPCs ex vivo at a temperature range of about 22° C. to about 39° C.; at a final concentration of about 10 μM to about 25 μM of a prostaglandin pathway agonist, for a duration of about 1 hour to about 4 hours, for about 2 hours to about 3 hours, for about 2 hours to about 4 hours, or for about 3 hours to about 4 hours.

In additional embodiments, hematopoietic cells having therapeutic potential have been modulated under conditions sufficient to increase gene expression of about 2, 5, 10, 25, 50, 75, or 100 signature genes at least 2, 3, 5, 10, 20, 30, 40, 50, 60, 70, or 80 fold in the modulated cells compared to control cells, the conditions comprising treating HSPCs ex vivo at a temperature range of about 22° C. to about 39° C.; at a final concentration of about 10 µM to about 25 µM of $PGE_2$ or $dmPGE_2$, for a duration of about 1 hour to about 4 hours, for about 2 hours to about 3 hours, for about 2 hours to about 4 hours, or for about 3 hours to about 4 hours.

In certain embodiments, hematopoietic cells having therapeutic potential have been modulated under conditions sufficient to increase gene expression of about 2, 5, 10, 25, 50, 75, or 100 signature genes at least 2, 3, 5, 10, 20, 30, 40, 50, 60, 70, or 80 fold in the modulated cells compared to control cells, said conditions comprising treating HSPCs ex vivo at a temperature range of about 22° C. to about 39° C.; at a final concentration of about 10 µM to about 25 µM of $PGE_2$ or $dmPGE_2$, for a duration of about 1 hour to about 4 hours, for about 2 hours to about 3 hours, for about 2 hours to about 4 hours, or for about 3 hours to about 4 hours.

In one embodiment, cell potency assays contemplated herein comprise determining, measuring, confirming, or validating the therapeutic potential of hematopoietic cells that have been modulated under conditions sufficient to increase gene expression of about 10 signature genes at least two-fold to at least three-fold in the modulated cells compared to control cells, said conditions comprising treating HSPCs ex vivo at a temperature range of about 22° C. to about 39° C.; at a final concentration of about 10 µM to about 25 µM of $PGE_2$ or $dmPGE_2$, for a duration of about 1 hour to about 4 hours, for about 2 hours to about 3 hours, for about 2 hours to about 4 hours, or for about 3 hours to about 4 hours.

In one embodiment, optimal therapeutic potential of a hematopoietic cell population is obtained by treating the cells ex vivo with 10 µM $PGE_2$ or $dmPGE_2$, at a temperature of about 37° C.; for a duration of about 2 hours.

F. Uses of Cells with Therapeutic Potential

Cells with therapeutic potential can be useful in a variety of clinical settings, including cell transplantation, treatment of hematological disorders, diseases, and conditions, treatment of ischemia, and gene therapy. In particular embodiments, hematopoietic cells, e.g., HSPCs, having therapeutic potential are useful in increasing engraftment, reconstitution, homing, and proliferation of cell grafts in a subject in need thereof.

"Subjects in need thereof" include, but are not limited to a subject in need of hematopoietic engraftment, reconstitution, homing, proliferation, or gene therapy. Included are subjects that have or that have been diagnosed with various types of leukemias, anemias, lymphomas, myelomas, immune deficiency disorders, and solid tumors as discussed elsewhere herein. A "subject" also includes a human who is a candidate for stem cell transplant or bone marrow transplantation, such as during the course of treatment for a malignant disease or a component of gene therapy. In particular embodiments, a subject receives genetically modified HSPCs as a cell-based gene therapy. Subjects may also include individuals or animals that donate stem cells or bone marrow for allogeneic transplantation. In certain embodiments, a subject may have undergone myeloablative irradiation therapy or chemotherapy, or may have experienced an acute radiation or chemical insult resulting in myeloablation. In certain embodiments, a subject may have undergone irradiation therapy or chemotherapy, such as during various cancer treatments. Typical subjects include animals that exhibit aberrant amounts (lower or higher amounts than a "normal" or "healthy" subject) of one or more physiological activities that can be modulated by an agent or a stem cell or marrow transplant.

Subjects in need of hematopoietic engraftment or reconstitution include subjects undergoing chemotherapy or radiation therapy for cancer, as well as subjects suffering from (e.g., afflicted with) non malignant blood disorders, particularly immunodeficiencies (e.g. SCID, Fanconi's anemia, severe aplastic anemia, or congenital hemoglobinopathies, or metabolic storage diseases, such as Hurler's disease, Hunter's disease, mannosidosis, among others) or cancer, particularly hematological malignancies, such as acute leukemia, chronic leukemia (myeloid or lymphoid), lymphoma (Hodgkin's or non-Hodgkin's), multiple myeloma, myelodysplastic syndrome, or non-hematological cancers such as solid tumors (including breast cancer, ovarian cancer, brain cancer, prostate cancer, lung cancer, colon cancer, skin cancer, liver cancer, or pancreatic cancer).

Subjects also include subjects suffering from aplastic anemia, an immune disorder (severe combined immune deficiency syndrome or lupus), myelodysplasia, thalassemaia, sickle-cell disease or Wiskott-Aldrich syndrome. In some embodiments, the subject suffers from a disorder that is the result of an undesired side effect or complication of another primary treatment, such as radiation therapy, chemotherapy, or treatment with a bone marrow suppressive drug, such as zidovadine, chloramphenical or gangciclovir. Such disorders include neutropenias, anemias, thrombocytopenia, and immune dysfunction.

Other subjects may have disorders caused by an infection (e.g., viral infection, bacterial infection or fungal infection) which causes damage to stem or progenitor cells of the bone marrow.

In addition, subject suffering from the following conditions can also benefit from treatment using HSPCs of the invention: lymphocytopenia, lymphorrhea, lymphostasis, erythrocytopenia, erthrodegenerative disorders, erythroblastopenia, leukoerythroblastosis; erythroclasis, thalassemia, myelofibrosis, thrombocytopenia, disseminated intravascular coagulation (DIC), immune (autoimmune) thrombocytopenic purpura (ITP), HIV inducted ITP, myelodysplasia; thrombocytotic disease, thrombocytosis, congenital neutropenias (such as Kostmann's syndrome and Schwachman-Diamond syndrome), neoplastic associated-neutropenias, childhood and adult cyclic neutropaenia; post-infective neutropaenia; myelodysplastic syndrome; neutropaenia associated with chemotherapy and radiotherapy; chronic granulomatous disease; mucopolysaccharidoses; Diamond Blackfan; Sickle cell disease; Beta thalassemia major; Gaucher's disease; Krabbe's disease; metachromatic leukodystrophy; Tay-Sachs; Nieman Pick; glycoproteinoses (e.g., fucosidosis, a-mannosidosis); and MPS-III (Sanfillipo).

In a particular embodiment, the subject is a bone marrow donor who has donated bone marrow, is a bone marrow donor who has yet to donate bone marrow, is a bone marrow donor transplant recipient, has hematopoietic progenitor cells under environmental stress, has anemia, has a reduced level of immune cell function compared to a normal subject, or has an immune system deficiency.

In a certain embodiment, the subject has myeloma, non-Hodgkin's lymphoma, Hodgkin's lymphoma, chronic myeloid leukemia, chronic myelogenous leukemia, chronic granulocytic leukemia, acute lymphoblastic leukemia, acute nonlymphoblastic leukemia, or pre-leukemia.

Subject also include those in need of treatment for ischemic tissue or one or more symptoms associated with tissue ischemia, including, but not limited to, impaired, or loss of, organ function (including without limitation impairments or loss of brain, kidney, or heart function), cramping, claudication, numbness, tingling, weakness, pain, reduced wound healing, inflammation, skin discoloration, and gangrene. As used herein, the terms "ischemia," "ischemic condition," or "ischemic event" mean any decrease or stoppage in the blood supply to any cell, tissue, organ, or body part caused by any constriction, damage, or obstruction of the vasculature. Ischemia sometimes results from vasoconstriction or thrombosis or embolism. Ischemia can lead to direct ischemic injury, tissue damage due to cell death caused by reduced supply of oxygen (hypoxia, anoxia), glucose, and nutrients. "Hypoxia" or a "hypoxic condition" intends a condition under which a cell, organ or tissue receives an inadequate supply of oxygen. "Anoxia" refers to a virtually complete absence of oxygen in the organ or tissue, which, if prolonged, may result in death of the cell, organ or tissue.

In particular embodiments, the subject is in need of gene therapy, such as, for example, a hemoglobinopathy. As used herein, the term "hemoglobinopathy" or "hemoglobinopathic condition" includes any disorder involving the presence of an abnormal hemoglobin molecule in the blood. Examples of hemoglobinopathies included, but are not limited to, hemoglobin C disease, hemoglobin sickle cell disease (SCD), sickle cell anemia, and thalassemias. Also included are hemoglobinopathies in which a combination of abnormal hemoglobins are present in the blood (e.g., sickle cell/Hb-C disease).

The term "sickle cell anemia" or "sickle cell disease" is defined herein to include any symptomatic anemic condition which results from sickling of red blood cells. Manifestations of sickle cell disease include: anemia; pain; and/or organ dysfunction, such as renal failure, retinopathy, acute-chest syndrome, ischemia, priapism and stroke. As used herein the term "sickle cell disease" refers to a variety of clinical problems attendant upon sickle cell anemia, especially in those subjects who are homozygotes for the sickle cell substitution in HbS. As used herein, the term "thalassemia" encompasses hereditary anemias that occur due to mutations affecting the synthesis of hemoglobin. Thus, the term includes any symptomatic anemia resulting from thalassemic conditions such as severe or β-thalassemia, thalassemia major, thalassemia intermedia, α-thalassemias such as hemoglobin H disease.

In one embodiment, a method of cell-based therapy, comprises administering to a subject in need thereof, a population of cells having sufficient therapeutic potential identified, confirmed, or validated using the cell potency assays contemplated herein. In various embodiments, the cells are hematopoietic cells, such as, for example, hematopoietic stem or progenitor cells (e.g., isolated from umbilical cord blood or mobilized peripheral blood), optionally treated with one or more agents to increase the therapeutic potential of the cells. In a certain embodiment, the hematopoietic cells are treated with a prostaglandin pathway agonist, e.g., 16,16-dmPGE$_2$, optionally at a concentration of 10 µM, for a time of about 2 hours, at 37° C.

In certain embodiments, cell potency assays contemplated herein identify, confirm, or validate cell populations with therapeutic potential that are then subsequently used in methods of increasing engraftment, homing, and/or reconstitution in a subject in need thereof. In one embodiment, a method of increasing engraftment, homing, and/or reconstitution comprises administering to a subject in need thereof, a population of cells having sufficient therapeutic potential identified, confirmed, or validated using the cell potency assays contemplated herein. In various embodiments, the cells are hematopoietic cells, such as, for example, hematopoietic stem or progenitor cells (e.g., isolated from umbilical cord blood or mobilized peripheral blood), optionally treated with one or more agents to increase the therapeutic potential of the cells. In a certain embodiment, the hematopoietic cells are treated with a prostaglandin pathway agonist, e.g., 16,16-dmPGE$_2$, optionally at a concentration of 10 µM, for a time of about 2 hours, at 37° C.

Administration of an "amount" of cells having therapeutic potential to a subject refers to administration of "an amount effective," to achieve the desired therapeutic or prophylactic result, including without limitation, treatment of the subject. A "therapeutically effective amount" of cells for purposes herein is thus determined by such considerations as are known in the art, and may vary according to factors such as the disease state, age, sex, and weight of the individual, and the ability of the cells to elicit a desired response in the individual. The term "therapeutically effective amount" includes an amount that is effective to "treat" a subject (e.g., a patient). A therapeutically effective amount is also one in which any toxic or detrimental effects of the cells are outweighed by the therapeutically beneficial effects.

A "prophylactically effective amount" refers to an amount of cells having therapeutic potential that is effective to achieve the desired prophylactic result. Typically but not necessarily, since a prophylactic dose is used in subjects prior to or at an earlier stage of disease, the prophylactically effective amount is less than the therapeutically effective amount.

Suitable methods for administering populations of cells used in the methods described herein include parenteral administration, including, but not limited to methods of intravascular administration, such as intravenous and intraarterial administration. Additional illustrative methods for administering cells of the invention include intramuscular, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Particular embodiments of the present invention now will be described more fully by the following examples. This invention may, however, be embodied in many different forms and should not be construed as limited to the embodiments set forth herein; rather, these embodiments are provided so that this disclosure will be thorough and complete, and will fully convey the scope of the invention to those skilled in the art.

EXAMPLES

Example 1

Cell Potency Assays

Methods

An outline of the cell potency assay is shown in FIG. 1. Human umbilical cord blood was treated ex vivo with 16,16, dimethyl prostaglandin E2 (dmPGE2) prior to transplantation. Real-time PCR transcript quantitation of gene expression from the treated cord blood cells was used to determine the therapeutic potential of the cells. RNA was extracted from an aliquot (100 uL) of the treated cord blood cells using the PicoPure RNA Isolation kit (Life Technologies) using the manufacturer's recommended protocol. Total RNA was quantified using the Nanodrop 2000 Spectrophotometer (Thermo Scientific). Complimentary DNA (cDNA) was reverse transcribed from 50 ng of total RNA using the High-Capacity cDNA Reverse Transcription Kit (Life Technologies).

Amplification of specific target cDNAs was performed using 14 cycles of amplification according to the manufacturer's protocol with a 200 nM pooled set of pre-designed TaqMan assays (Life Technologies) for the following signature genes: CXCR4 (Hs00976734_m1), CREM (Hs01590456-m1), CXCL2 (Hs00601975-m1), CXCL3 (Hs00171061-m1), GEM (Hs00738924-m1), HEY1 (Hs01114113-m1), NR4A2 (Hs00428691-m1), NR4A3 (Hs00545007-m1), IL1A (Hs00174092-m1), PTGS2 (Hs00153133-m1), ULBP2 (Hs00607609-mH), HPRT1 (Hs01003267-m1), and GAPDH (Hs99999905-m1).

Quantitative PCR was performed in triplicate for each gene in the amplified cDNA using StepOne Plus (Applied Biosystems) and Taqman gene expression assays (Life Technologies) and 40 cycles of real-time PCR. Results of the real-time PCR were analyzed using the StepOne Software v2.1 analysis package (Applied Biosystems). Expression values of the transcripts were normalized to the Taqman gene expression average for the housekeeping genes, GAPDH and HPRT1, to determine the relative expression levels (ΔCt values).

A score is given based on the correlation (standardized Euclidean distance) of expression levels of all the genes in comparison to a reference training set of control treated umbilical cord blood samples and ex vivo enhanced umbilical cord blood samples. Scores with positive values cluster more closely with ex vivo enhanced samples, while negative scores group with the control samples.

Results

Figure 2:
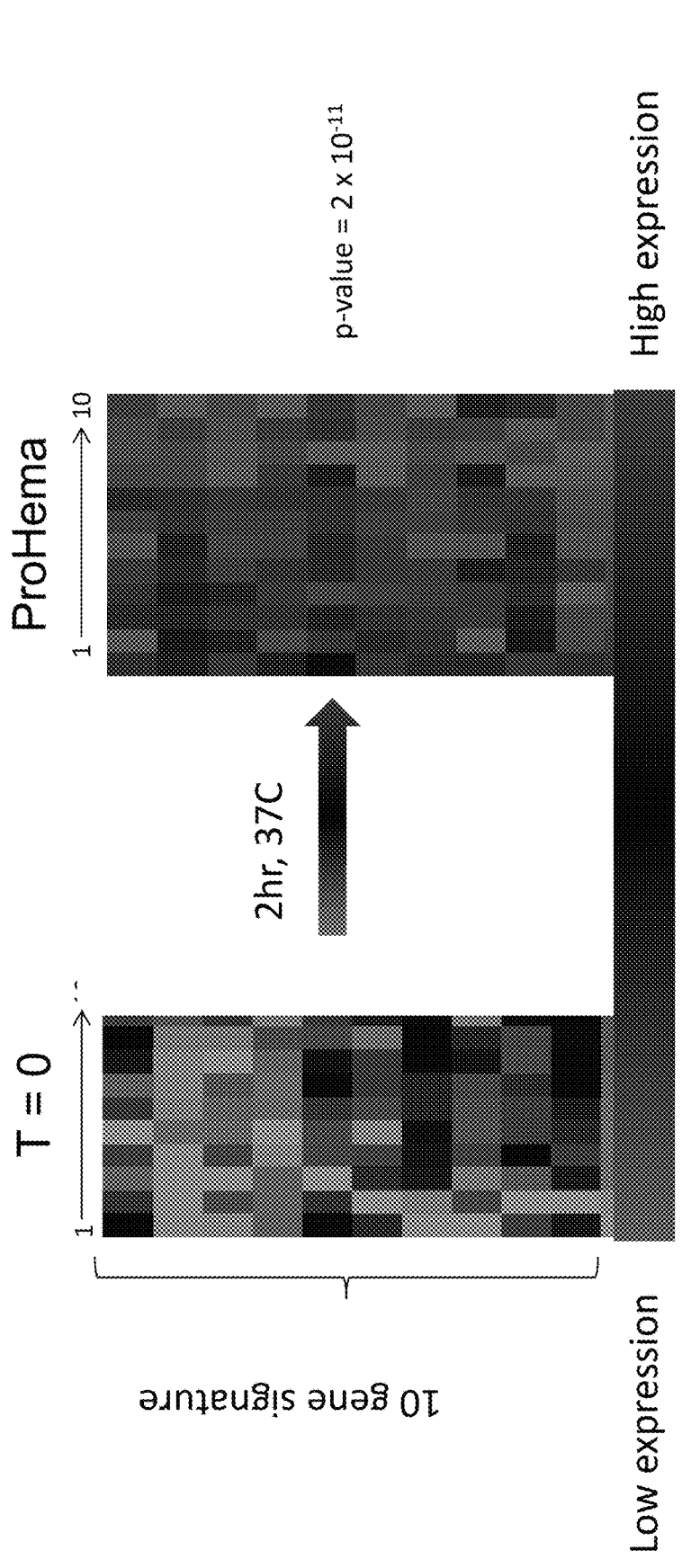
FIG. 2 shows how changes in gene expression are used to calculate a gene expression score.
Figure 3:
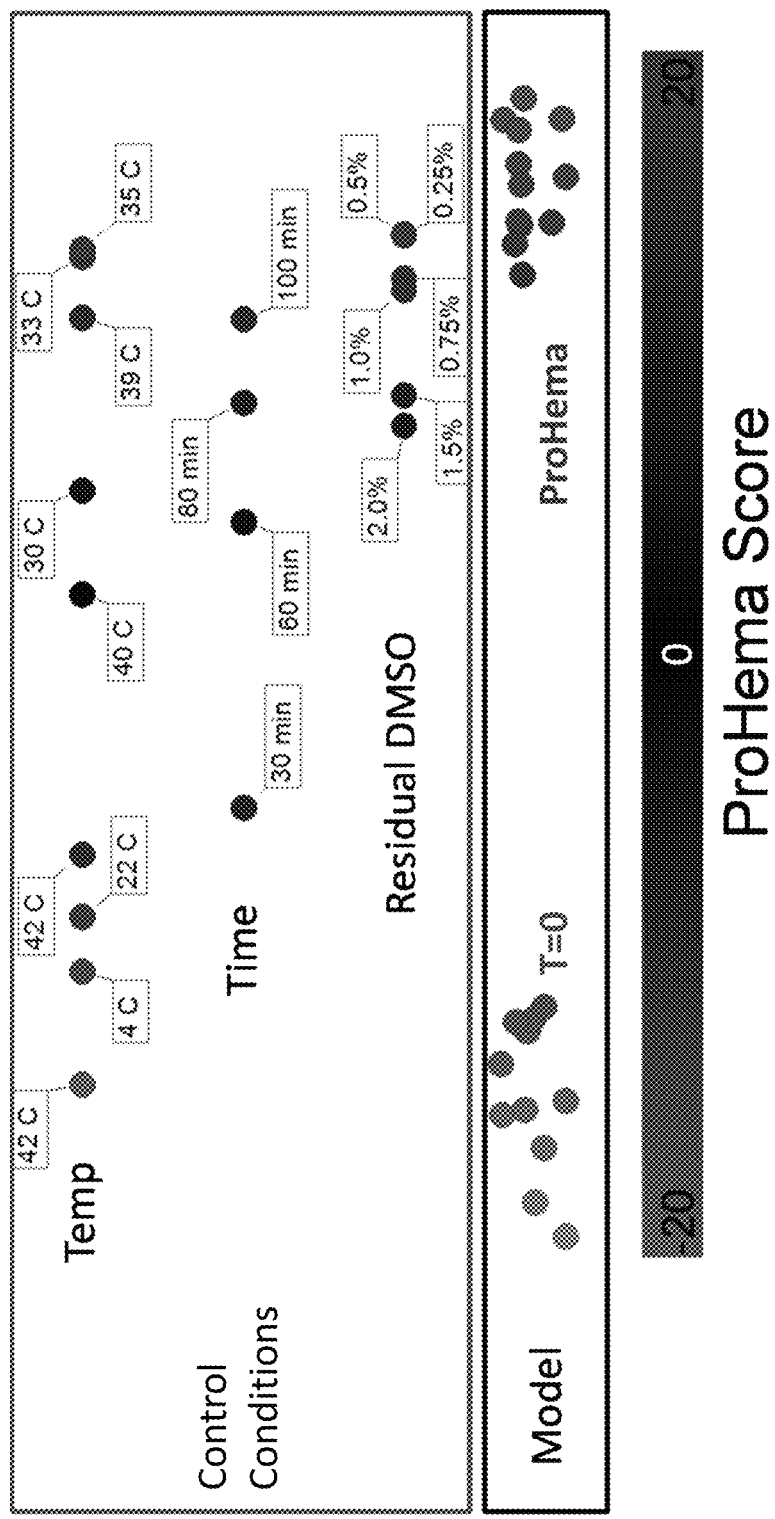
FIG. 3 shows an example of how the gene expression scores are able to identify hematopoietic cell populations with therapeutic potential compared control cell populations.

Increased gene expression in the group of signature genes was observed in human umbilical cord blood after a two hour treatment with dmPGE2. The increase in gene expression was measured with real-time PCR and compared to a validated training set of results using standardized Euclidean distance models to determine if the cells had sufficient therapeutic potential. FIG. 2. Results of the model gave positive scores (16.8+/−2.2 SD) where dmPGE2 treated test samples (n=10) cluster more closely with the training set of ex vivo samples having therapeutic potential, while control test samples (n=10) gave negative scores (−17.8+/−3.0 SD) and cluster with the control samples that lack therapeutic potential. Umbilical cord blood samples that were not treated under the ideal conditions (about two hours at 37° C. with 10 μM dmPGE2) gave variable scores in the middle indicating sub-optimal or insufficient therapeutic potential. FIG. 3.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for treating a subject in need of cell based therapy with a population of hematopoietic cells having therapeutic potential comprising:
   a) validating therapeutic potential of the cell population by:
      i) measuring expression of a plurality of signature genes in the cell population;
      ii) calculating a score using gene expression clustering of expression measured for the plurality of signature genes in said cell population to expression measured for the plurality of signature genes in control cells that lack therapeutic potential and to expression measured for the plurality of signature genes in control cells with optimal therapeutic potential; and
      iii) identifying the cell population as having therapeutic potential if the score is greater than or equal to a predetermined cut-off value, and
   b) administering a therapeutically effective amount of the cell population having therapeutic potential to the subject;
   wherein the plurality of signature genes comprises cAMP-responsive element modulator (CREM), GTP-binding protein GEM (GEM), nuclear receptor subfamily 4, group A, member 2 (NR4A2), nuclear receptor subfamily 4, group A, member 3 (NR4A3), interleukin IA (ILIA), hairy/enhancer-of-split related with YRPW motif 1 (HEY1), chemokine (C-X-C motif) ligand 2 (CXCL2), chemokine (C-X-C motif) ligand 3 (CXCL3), and UL16 binding protein 2 (ULBP2).

2. The method of claim 1, wherein the population of hematopoietic cells is bone marrow cells (BMCs), umbilical cord blood cells (UCBCs), placental blood cells, mobilized peripheral blood cells (MPBCs), hematopoietic stem cells (HSCs), hematopoietic progenitor cells (HPCs), or CD34+ cells.

3. The method of claim 1, wherein at least a portion of the cells is expanded ex vivo prior to measuring expression of the plurality of genes.

4. The method of claim 1, wherein at least a portion of the cells is cryopreserved prior to measuring expression of the plurality of genes.

5. The method of claim 2, wherein the hematopoietic cells are modulated ex vivo prior to measuring expression of the plurality of genes by contacting the population of hematopoietic cells with at least one agent selected from the group consisting of a cAMP analogue or enhancer, a Ga-s activator, and a prostaglandin pathway agonist.

6. The method of claim 5, wherein the prostaglandin pathway agonist selectively binds a prostaglandin $E_2$ receptor 2 ($PGE_2$ $EP_2$) or a prostaglandin $E_2$ receptor 4 ($PGE_2$ $EP_4$) receptor.

7. The method of claim 5, wherein the prostaglandin pathway agonist comprises prostaglandin $E_2$ ($PGE_2$), or a $PGE_2$ analogue or derivative.

8. The method of claim 5, wherein the prostaglandin pathway agonist is selected from the group consisting of: prostaglandin $E_2$ ($PGE_2$), 16,16-dimethyl $PGE_2$ (16,16- dmPGE$_2$), 15(S)-15-methyl PGE$_2$, 20-ethyl PGE$_2$, and 8-iso-16-cyclohexyl-tetranor PGE$_2$.

9. The method of claim 5, wherein the prostaglandin pathway agonist comprises 16,16-dimethyl PGE$_2$ (16,16-dmPGE$_2$).

10. The method of claim 5, wherein the hematopoietic cells are further contacted with a glucocorticoid.

11. The method of claim 5, w herein the cells are modulated ex vivo by contacting the population of cells with the at least one agent for a time of about one hour to about 24 hours.

12. The method of claim 11, w herein the cells have been contacted with the at least one agent at a temperature of about 37° C. for at least two hours.

13. The method of claim 11, wherein the cells have been contacted with the at least one agent at a temperature of about 25° C. to about 37° C.

14. The method of claim 1, wherein expression of at least two of the plurality of genes is increased by about 2-fold to about 20-fold compared to expression of the at least two of the plurality of genes in a control population of cells.

15. The method of claim 1, w herein the subject in need has a disease, disorder, or condition selected from the group consisting of: ischemia, a non malignant blood disorder, an immunodeficiency, severe combined immunodeficiency (SCID), lymphocytopenia, thrombocytopenia, neutropenia, anemia, Fanconi's anemia, severe aplastic anemia, a congenital hemoglobinopathy, sickle cell disease, β-thalassemia, Wiskott-Aldrich syndrome, a metabolic storage disease, Hurler's disease, Hunter's disease, mannosidosis, a cancer, a hematological malignancy, acute leukemia, chronic myeloid leukemia, chronic lymphoid leukemia, Hodgkin's lymphoma, non-Hodgkin's lymphoma, multiple myeloma, myelodysplastic syndrome, a non-hematological cancer, breast cancer, ovarian cancer, brain cancer, prostate cancer, lung cancer, colon cancer, skin cancer, liver cancer, pancreatic cancer, Gaucher's disease, Krabbe's disease, metachromatic leukodystrophy, Tay-Sachs, Nieman Pick, glycoproteinoses, and MPS-III (Sanfillipo).

16. The method of claim 1, wherein the method increases hematopoietic reconstitution and/or engraftment in the subject.

17. The method of claim 1, wherein the pre-determined cut-off is based on the therapeutic properties observed from at least twenty test samples.

18. The method of claim 1, wherein said method controls quality of the cells for transplantation.

19. The method of claim 1, wherein the plurality of genes further comprises one or more of chemokine (C-X-C motif) receptor 4 (CXCR4), prostaglandin-endoperoxide synthase 2 (PTGS2), and cyclooxygenase 2 (COX2).

20. The method of claim 19, wherein if the cell population is identified as having therapeutic potential, the cell population is efficacious in treating a subject in need of cell-based therapy.

* * * * *